United States Patent
Shokrollahi et al.

(10) Patent No.: US 6,200,266 B1
(45) Date of Patent: Mar. 13, 2001

(54) METHOD AND APPARATUS FOR ULTRASOUND IMAGING USING ACOUSTIC IMPEDANCE RECONSTRUCTION

(75) Inventors: Nima Shokrollahi, Euclid; William Tobocman, Cleveland Heights, both of OH (US); Sanford Roth, New York, NY (US); Joseph Izatt, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/282,215

(22) Filed: Mar. 31, 1999

Related U.S. Application Data
(60) Provisional application No. 60/080,183, filed on Mar. 31, 1998.

(51) Int. Cl.⁷ .................................................. A61B 8/00
(52) U.S. Cl. .............................................................. 600/438
(58) Field of Search ..................................... 600/438, 443, 600/447, 448; 73/602

(56) References Cited

U.S. PATENT DOCUMENTS

| | | | |
|---|---|---|---|
| 4,063,549 | * 12/1977 | Beretsky et al. | 128/2 V |
| 4,545,250 | * 10/1985 | Miwa | 73/602 |
| 4,893,629 | * 1/1990 | Lewis | 600/443 |
| 5,435,312 | * 7/1995 | Spivey et al. | 600/448 |
| 5,445,155 | * 8/1995 | Sieben | 600/443 |
| 5,902,240 | * 5/1999 | Ishii et al. | 600/438 |

* cited by examiner

Primary Examiner—Marvin M. Lateef
Assistant Examiner—Ali M. Imam

(57) ABSTRACT

An ultrasound imaging system employs acoustic impedance reconstruction to produce high-resolution images of anatomical structures, which are virtually free of speckle. Determination of the acoustic impedance profile involves prefiltering of the incident ultrasound signal and the ultrasound signal reflected from the specimen to be imaged. A time domain window function is applied to both the incident and reflected signals, and an N-point FFT is computed for both the digitized incident and reflected signals to obtain the incident and reflected spectrums. A complex division of the reflected spectrum by the incident spectrum is performed to obtain the transfer function. A window function having a sharp, low-frequency cutoff is applied to the transfer function prior to performing an inverse FFT to obtain the estimated impulse response. The acoustic impedance of individual A-scans is calculated from the impulse response using the plane wave Born approximation, involving integration and exponentiation of the estimated impulse response. By mechanically or electronically scanning the transducer along a line, a series of A-scan acoustic impedance profiles are calculated and used to produce a two-dimensional, grey-scale B-scan image.

42 Claims, 29 Drawing Sheets

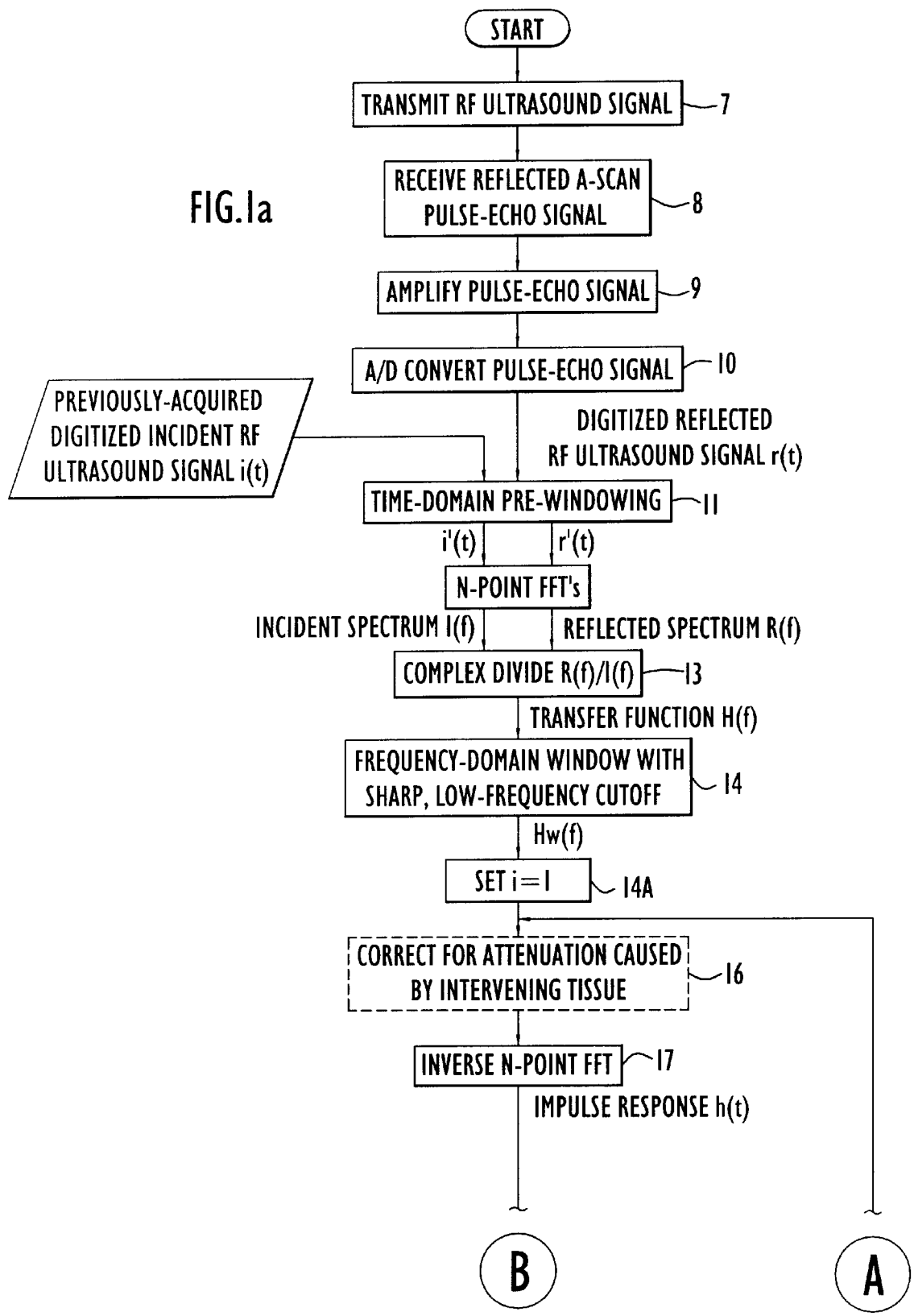

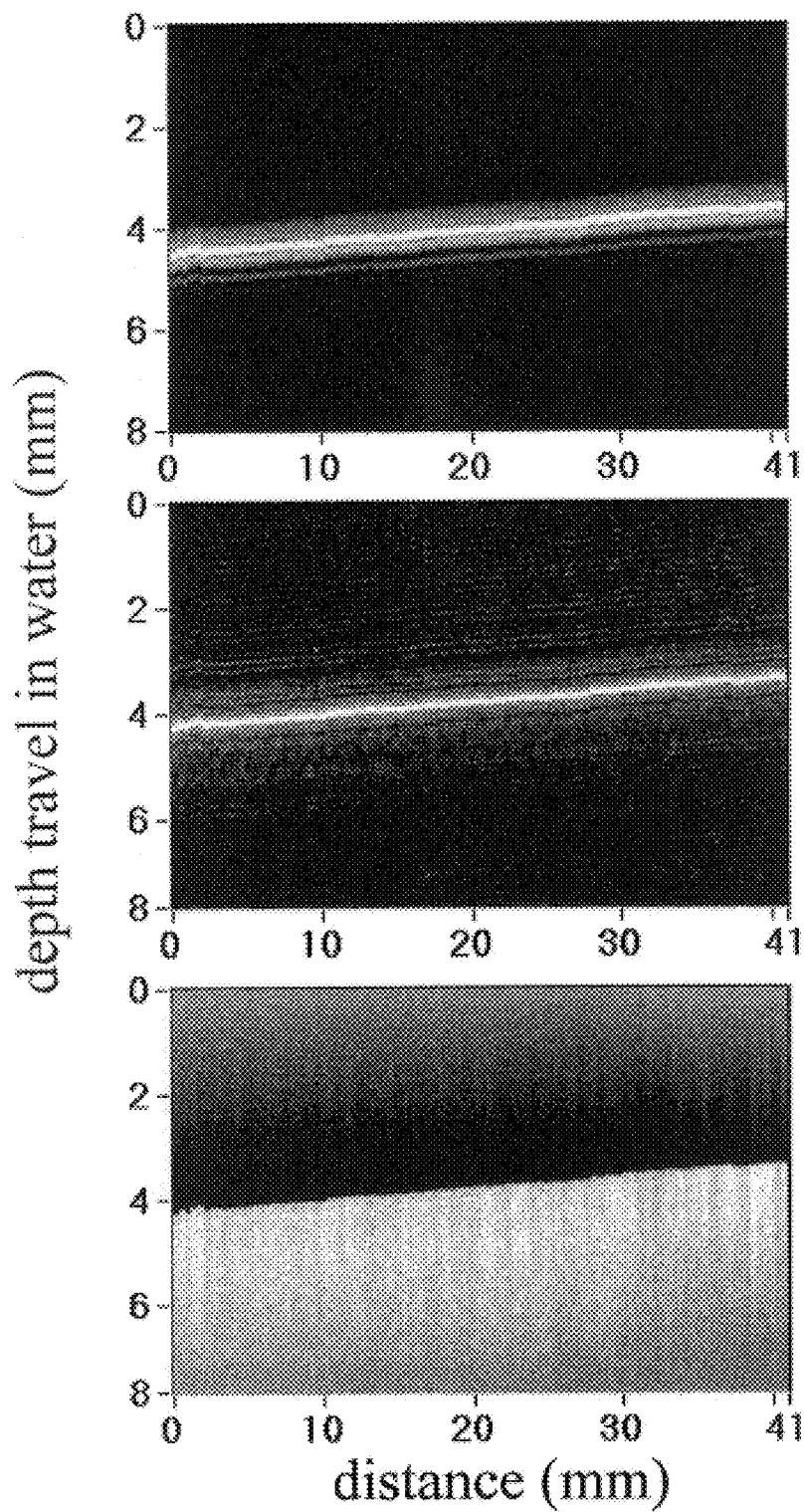

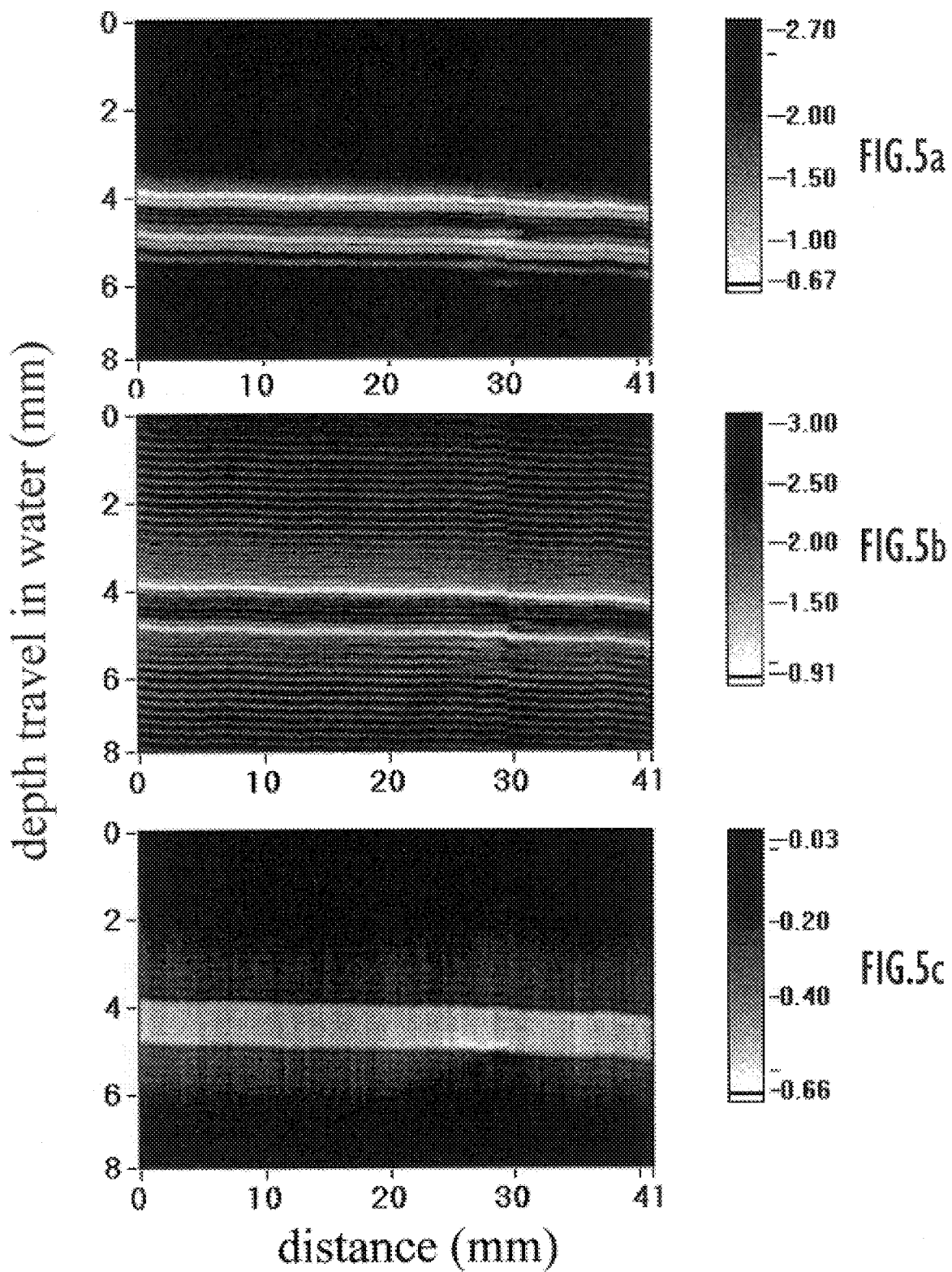

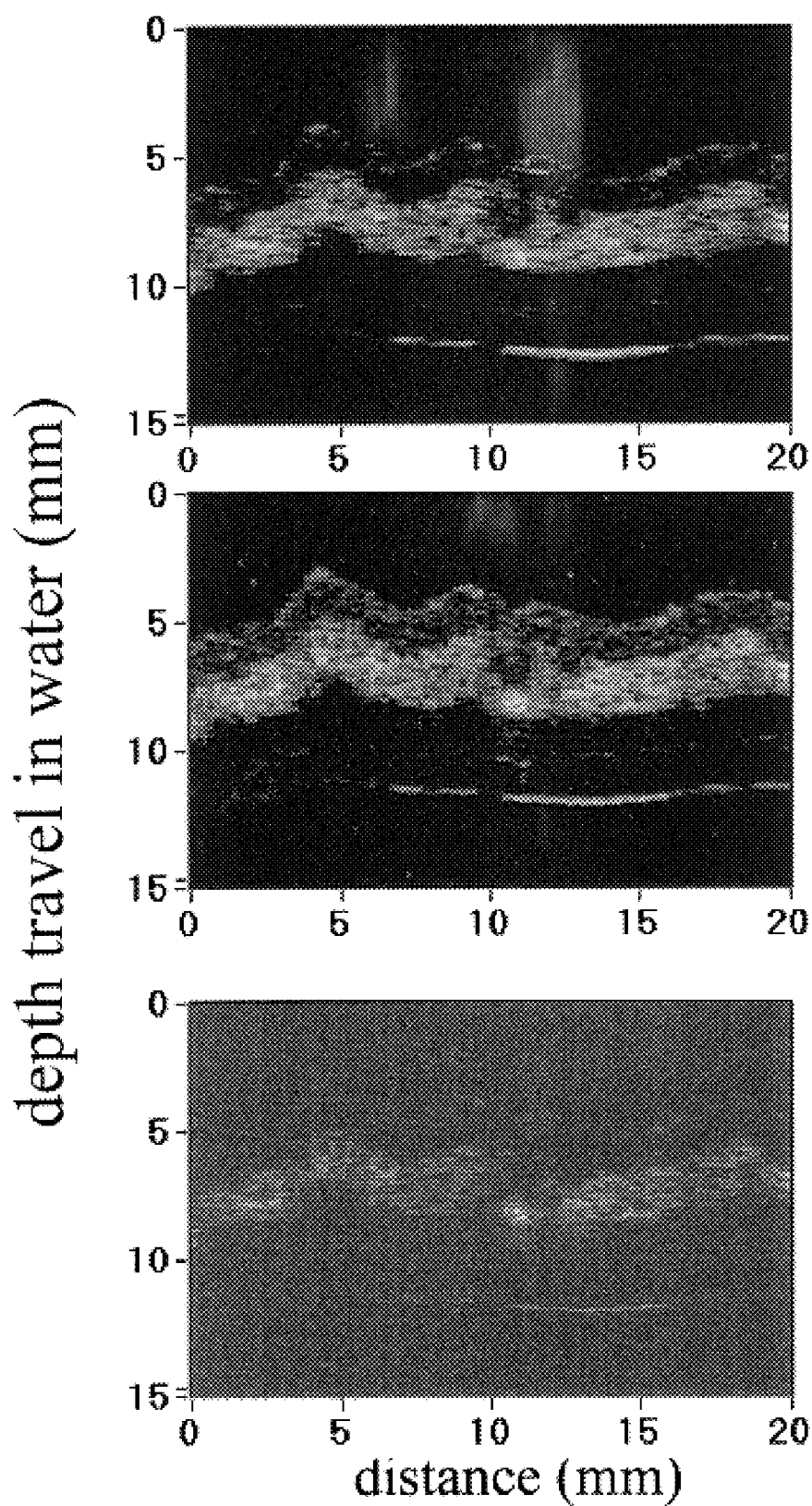

FIG.16a Pulse-echo FIG.16b
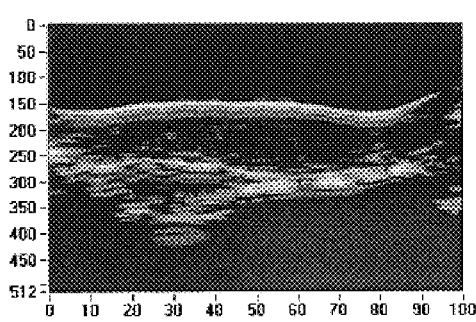 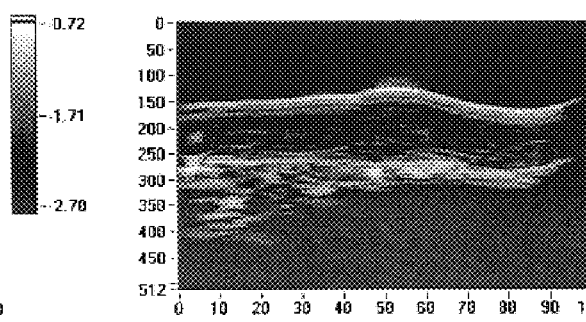
FIG.16c Acoustic impedance FIG.16d
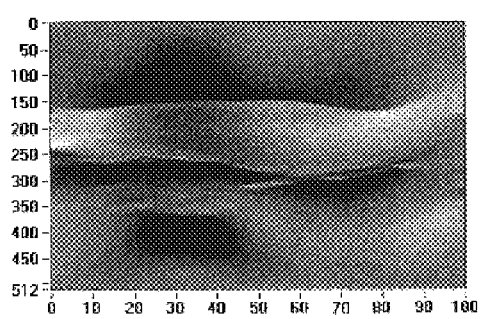 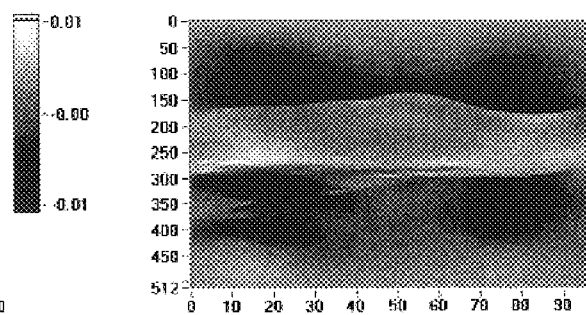

FIG.17a Pulse-echo FIG.17b
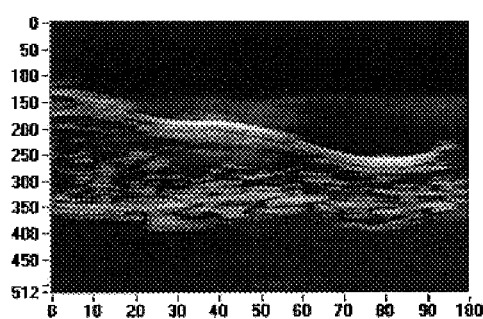 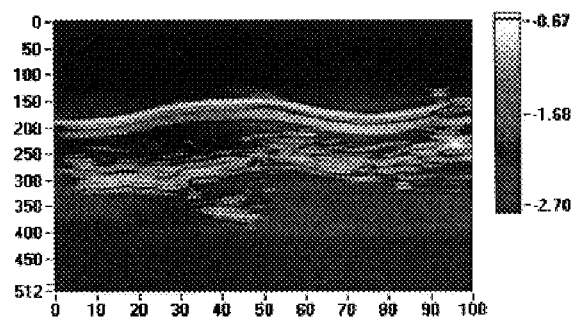
Acoustic impedance
FIG.17c FIG.17d
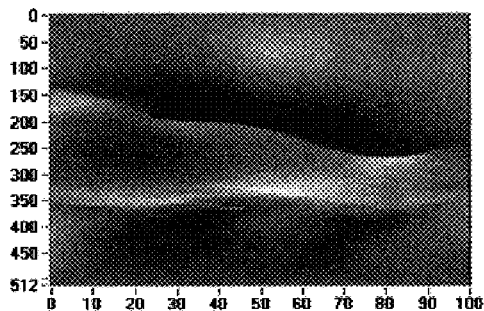 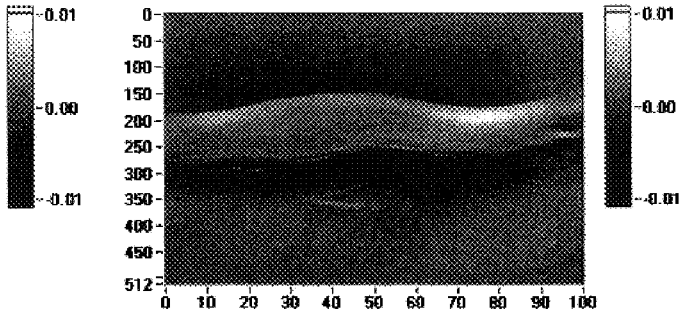

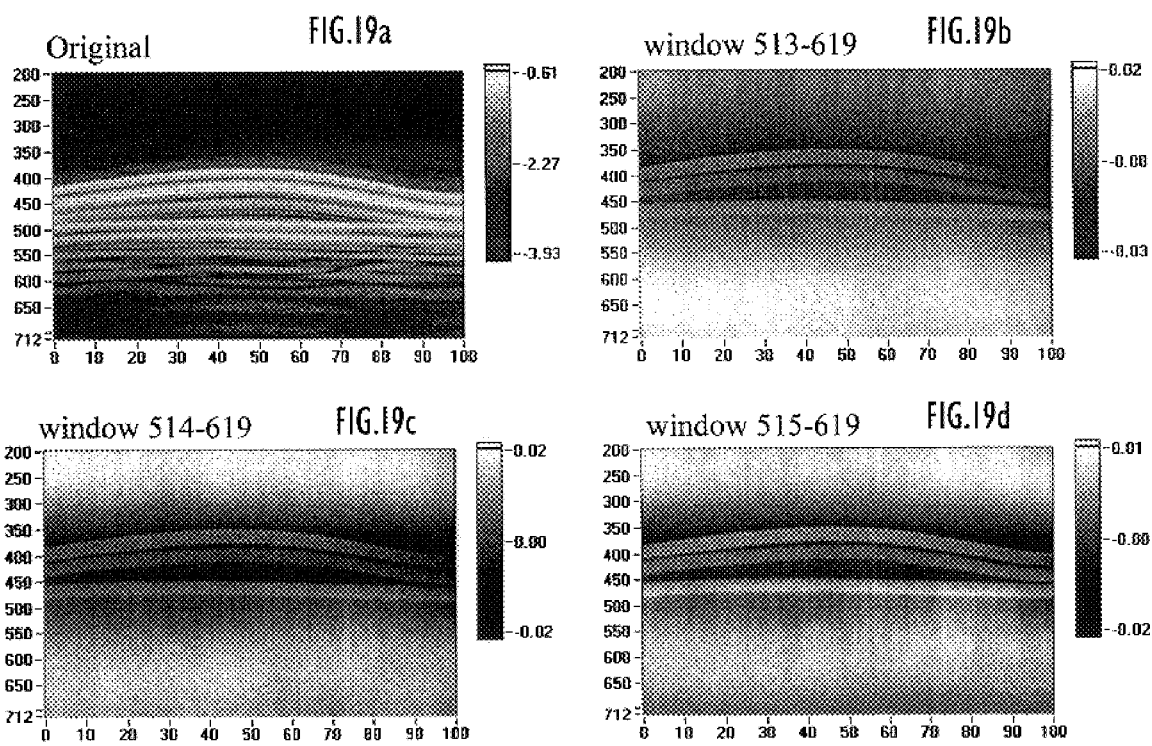

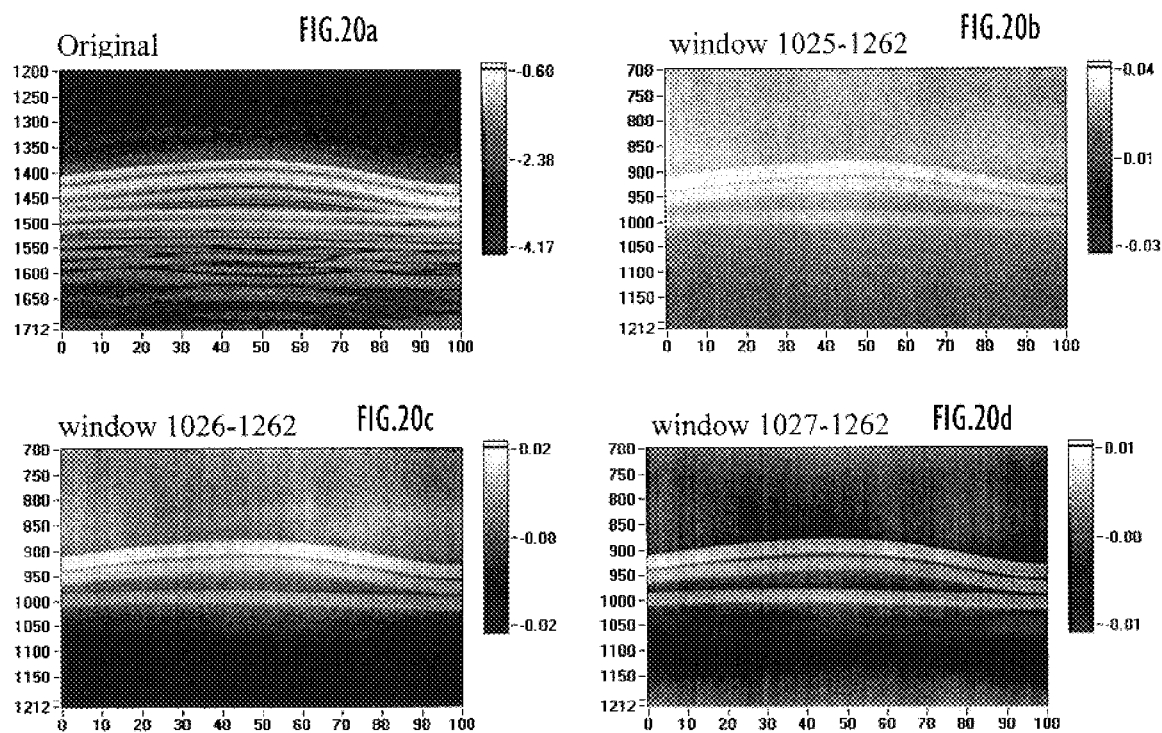

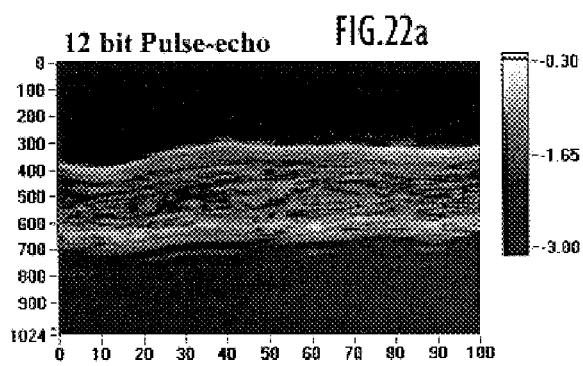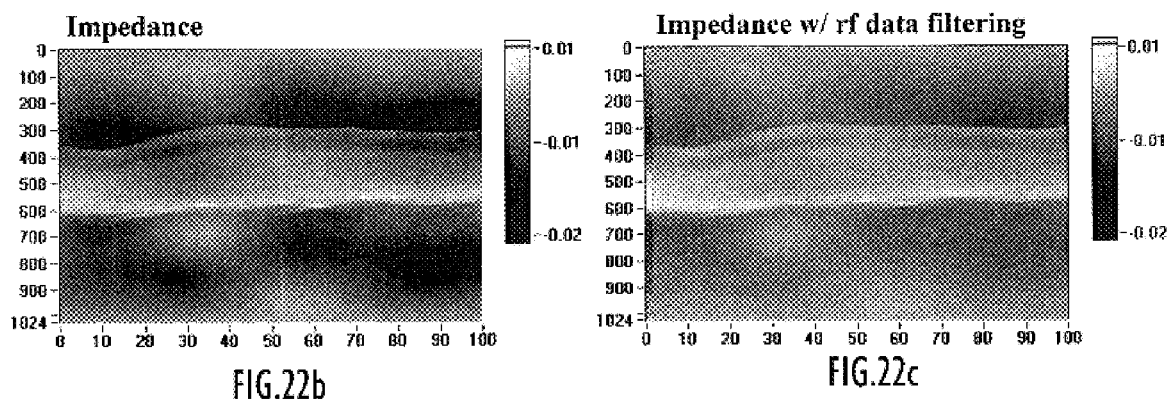

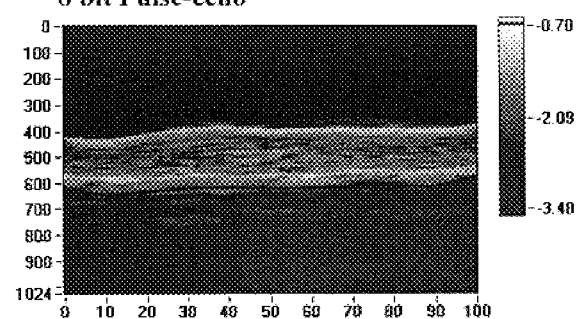
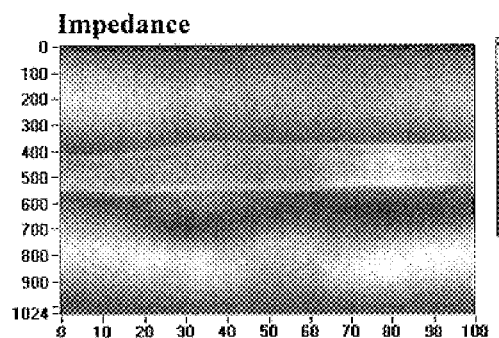
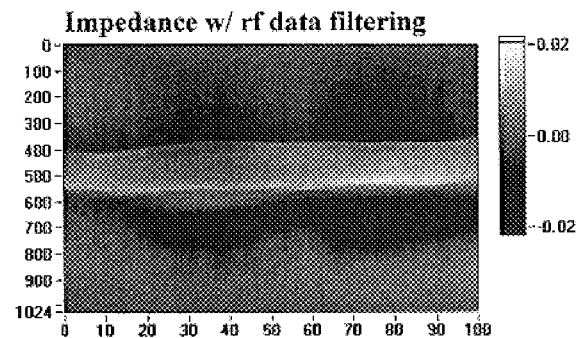
FIG.23a — 8 bit Pulse-echo
FIG.23b — Impedance
FIG.23c — Impedance w/ rf data filtering

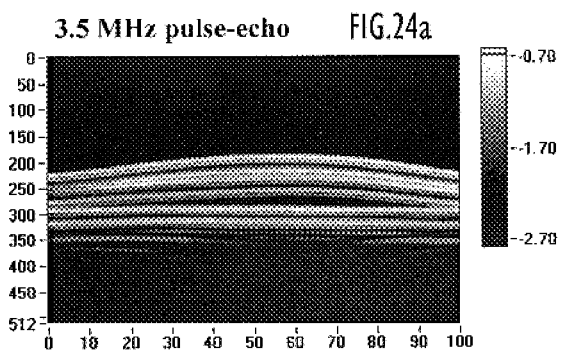
FIG.24a  3.5 MHz pulse-echo
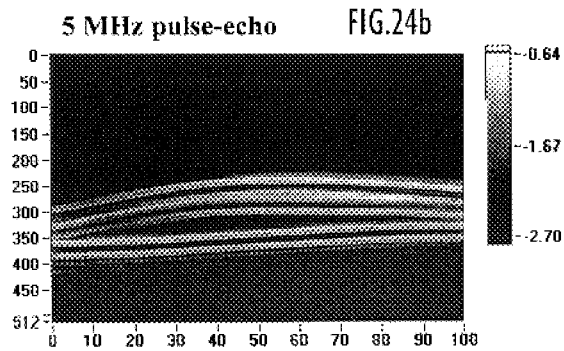
FIG.24b  5 MHz pulse-echo
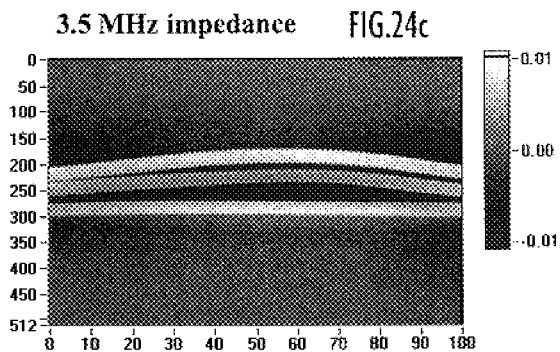
FIG.24c  3.5 MHz impedance
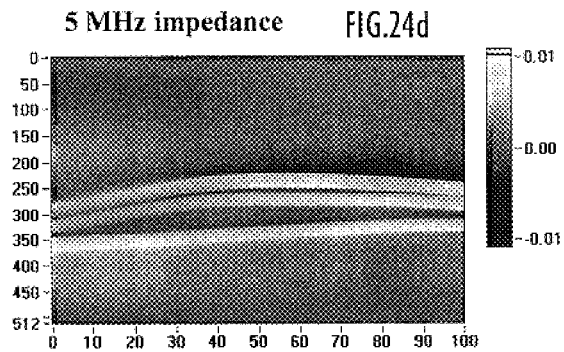
FIG.24d  5 MHz impedance

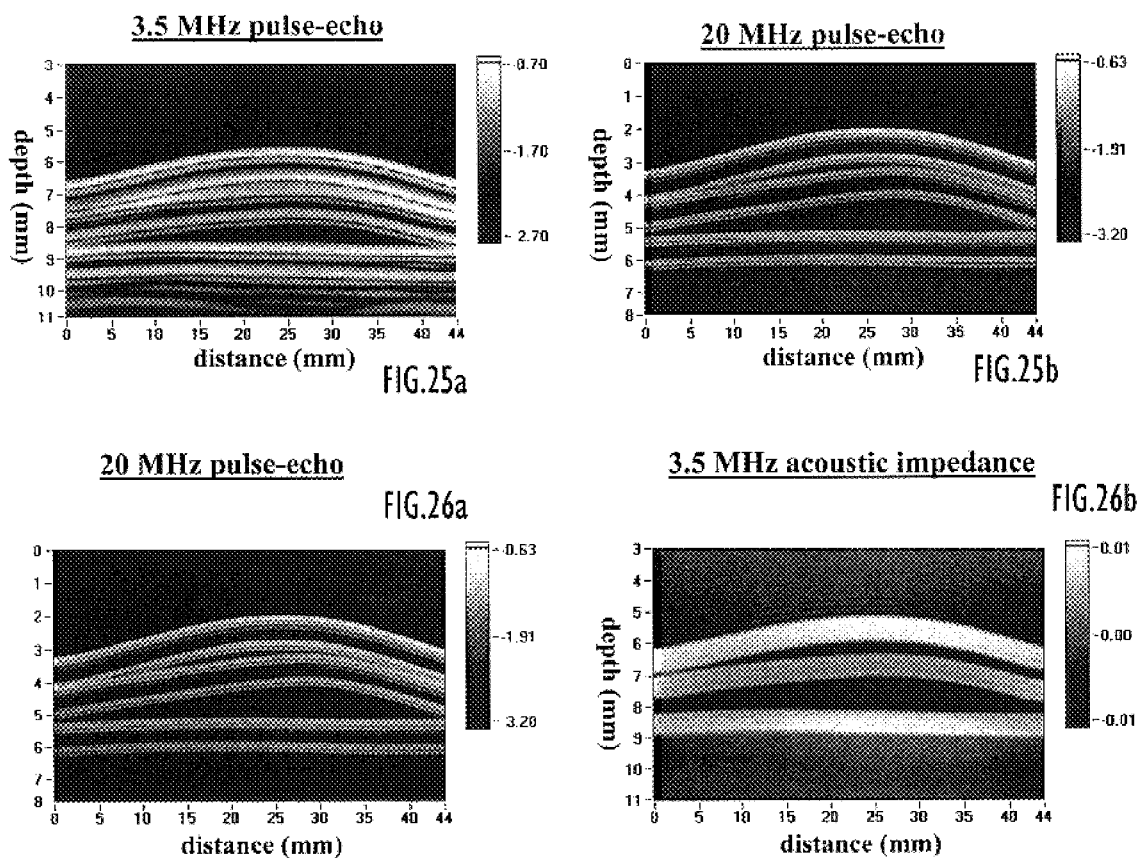

I - thin intima
M - media
L - lumen

T - intimal
    thickining

Histology section from imaged region

METHOD AND APPARATUS FOR ULTRASOUND IMAGING USING ACOUSTIC IMPEDANCE RECONSTRUCTION

This application claim benefit to provisional Application 60/080,183 Mar. 31, 1998.

BACKGROUND OF THE INVENTION

1. Field of the Invention

The present invention relates to a medical ultrasound imaging system for producing images of anatomic structures. In particular, the present invention relates to an ultrasound imaging system capable of producing and displaying the acoustic impedance of soft tissue, bone and the like, reconstructed from reflected pulse-echo ultrasound signals.

2. Description of the Related Art

Diagnostic imaging, based on technologies such as MRI, X-ray, CT and ultrasound, is currently performed by large, expensive equipment that often requires the patient to be brought considerable distances to special facilities. Although these techniques are non-invasive, some generate hazardous radiation that necessitates separation of the physician and technician from the patient during the procedure. Often, resolution and the ability to define a specific area under test are not satisfactory, making diagnosis difficult without further invasive exploration.

The availability of a convenient and cost-effective method to image and quantitatively assess the real time status of internal injuries, growths and fractures or other defects, and to identify and define the trauma site and trauma status, would be a valuable clinical tool. It could potentially shorten hospital stays and allow earlier return to normal activities. Further, it could provide early detection of malignancies and delayed fractures or non-union of fractures, thereby allowing early introduction of appropriate therapies. This could have a considerable economic impact in those cases where long-term disability could be avoided or minimized. If such a system were available at a moderate cost, it would potentially find use in the majority of medical offices, clinics and hospitals dealing with fractures and soft tissue injuries as well as in other medical fields, including physical therapy, sports medicine, rehabilitation and geriatrics.

Consequently, there has been a growing interest in recent years to develop higher resolution ultrasound imaging systems designed for specific applications. For example, a non-invasive diagnostic imaging technique capable of identifying malignancy in vivo would have a major impact on the detection and treatment of cancer. In dermatologic diagnostics, high resolution ultrasound systems have been developed utilizing transducer frequencies up to 100 MHz for imaging the layers of the skin, determining margins of small skin lesions, and characterizing non-malignant skin diseases by thickness measurements. In ophthalmology applications, such as characterization of ocular tissue, examination of eye tumors and assessment of corneal diseases, high frequency ultrasound systems have been developed approaching resolutions of 20 $\mu$m. Another ultrasound application of interest is that of imaging the gastrointestinal (GI) tract, where an endoscopic device can potentially be used to image gastrointestinal mucosa layers and layers of the esophageal wall and to detect and evaluate gastric tumors and lesions.

The currently employed pulse-echo method of ultrasound imaging provides a display of signals backscattered from tissue and has proven to be the most useful ultrasound method in medical applications to date. While higher signal frequencies generally yield higher image resolution, further improvement in resolution of ultrasound imaging of biological tissue is a challenging problem because of the increased attenuation suffered by the ultrasound signal with increasing frequency. The propagation of an ultrasound pressure beam through tissue causes the pressure beam to attenuate as a function of depth primarily due to absorption and scattering. Specifically, the propagation of an ultrasound pressure wave through a medium will result in the exponential decrease of the acoustic pressure amplitude parameter as a function of propagating distance. Several factors contribute to attenuation, the most important being absorption and scattering. Neglecting other losses such as beam spreading and diffraction, attenuation is described by the following expression:

$$A(x) = A_0 e^{-\mu x} \quad (1)$$

where x is the propagating distance in cm, $\mu$ is the amplitude attenuation coefficient, $A_0$ is the unattenuated amplitude, and A is the attenuated amplitude. The amplitude attenuation coefficient is a function frequency and is approximately given by:

$$\mu = \alpha f^n \quad (2)$$

where $\alpha$ is the weakly frequency dependent amplitude attenuation coefficient of the medium in units of Nepers/cm/Hz, and n is the exponent of the frequency dependence.

The frequency dependence of attenuation has an important effect on the spectrum of the propagating pulse. The higher frequencies are disproportionately attenuated, causing the spectrum of the traveling pulse to shift toward lower frequencies with increasing propagating distance. An approximate expression for the downshifted peak frequency in the spectrum of an ultrasound pulse traveling in water, where the exponent of frequency dependence is n=2, is given by:

$$f_p(x) = \frac{f_0}{2 \alpha x \sigma^2 + 1} \quad (4)$$

where $f_0$ is the peak frequency in the spectrum of the unattenuated pulse, and $f_p$ is the peak frequency in the spectrum of the attenuated pulse after it has propagated a distance x in the medium. The term $\sigma$ is given by:

$$\sigma = \frac{f_0 B}{236} \quad (5)$$

where B is Full Width Half Maximum (FWHM) bandwidth of the unattenuated spectrum expressed as a percentage.

For water, the exponent of frequency dependence is n=2; however, many soft tissues of the body attenuate ultrasound to a similar degree, which is a nearly linear frequency dependence. This gives rise to the general rule of thumb for ultrasound attenuation in tissue which is approximately 1 dB per centimeter per megahertz for most soft tissues.

Absorption results in the conversion of the pressure wave energy to heat and is responsible for the temperature rise made use of in ultrasound-induced hypothermia. The absorption mechanisms of ultrasound in biological tissue are quite complex. The mechanisms by which absorption can occur can be classified in three categories: classical mechanisms, molecular relaxation, and relative motion losses.

Classical absorption describes the frictional loss associated with a viscous medium. It has been shown that, in air or water, classical absorption dominates and the absorption is approximately proportional to $f^2$, the square of the sound frequency. However, in biological tissue, it has been postulated by Wells in *Biomedical Ultrasonics,* Academic Press (1977), that the absorption is due to a relaxation mechanism associated with the molecules. The pressure fluctuations associated with the sound wave cause reversible alterations in molecular configuration and, because there are likely to be many such mechanisms simultaneously in action, produce a frequency dependence close to $f^1$. Relative motion losses, in which the sound wave induces a viscous or thermally damped movement of small-scale structural elements of tissue, are also possible mechanisms for absorption and could produce a frequency dependence of absorption between $f^1$ and $f^2$. For simple solutions of molecules, increasing molecular complexity results in increasing absorption. For tissues, a higher protein content, especially structural proteins such as collagen, or a lower water content is associated with greater absorption of ultrasound.

Scattering of ultrasound radiation can be classified into three regimes: scattering by particles which have radii, a, much larger than the incident wavelength ($a>>\lambda$); scattering by particles with radii on the order of the incident wavelength ($a\approx\lambda$) or "Mie scattering"; and scattering by particles with radii much smaller than the incident wavelength ($a<<\lambda$) or Rayleigh scattering.

For particle sizes much larger than the wavelength ($a>>\lambda$), specular reflection of sound will occur between two homogeneous media. The laws of reflection and Snell's law for refraction apply to predict the direction of the reflected and refracted sound wave.

For particles whose radii are on the order of the incident wavelength ($a\approx\lambda$), scattering is characterized by a variable frequency dependence. The scattering is highly anisotropic and interference of scattered waves gives rise to 20–30 dB fluctuations in measured scattered energy with angle, position, orientation, and frequency.

For particles whose radii are much smaller than the incident wavelength ($a<<\lambda$), the scattering of a wave by a single scatterer is described by the scattering cross-section, which is defined as the total power scattered by the particle per unit incident intensity. In general, Rayleigh scattering occurs for cells in solid tissues which contribute to frequency dependence of scattering in tissues and in blood. The scattering is weak, is proportional to the volume of the scatterer, and follows an $f^4$ frequency dependence.

In view of these effects, the use of higher frequency transducers generally improves the depth resolution capability but at a cost of lowering the depth of penetration over which an image can be acquired. With the possible exception of ultrasound applications which form images of tissue in the immediate vicinity of the transducer (e.g., the skin surface), this loss of depth penetration can be unacceptable. Thus, there is a need for a high resolution ultrasound system that does not unduly sacrifice depth penetration performance.

Another obstacle to further improvement of ultrasound imaging is the presence of speckle. Speckle is the fluctuations in the signal level caused by interference between waves received simultaneously from several scattering sources within a resolution cell (defined by the point spread function) of the ultrasound imaging system. The apparent received echo level can vary from a value of zero corresponding to complete destructive interference to a maximum value corresponding to complete constructive interference. The simultaneous arrival or integration of signals can also be a result of multiple scattering, high side lobe or grating lobe levels, and any factors (such as an inhomogeneous propagation medium) that distort the phase of the received wave across the receiving aperture. This phenomena is characteristic of any imaging system based on coherent forms of radiation, including ultrasound, optical and radar systems. A possible mechanism of speckle has been explained by the rough volume model. In this model, a region of the object (which is known as the resolution cell of the imaging system) is said to contain scattering structure too fine to be resolved as a result of several scatterers within the resolution cell.

The speckle pattern in an ultrasound image changes if a different part of the object is imaged, the scattering structure is viewed from a different angle, or a different combination of frequencies is used in forming the image. Speckle reduction methods rely on varying one or more of the above stated parameters to generate multiple images with uncorrelated speckle patterns. These images are then averaged to reduce the effects of the speckle pattern. In synthetic aperture radar (SAR) imaging, this is known as diversity or multilook processing. For electromagnetic radiation, speckle also changes with changing polarization. In ultrasound, image speckle can be reduced by generating several images with uncorrelated speckle patterns and then averaging them. The reduction in speckle is obtained at a cost of some loss in spatial resolution. A compromise between loss of spatial resolution and gain in contrast resolution can be achieved by averaging a number of partially decorrelated speckle patterns.

Spatial averaging has been applied over images obtained by translating the scan plane and averaging over several frames obtained from a real-time scanner, and this may be a good technique for anatomic structures that do not vary substantially in the direction across the scan plane.

Spatial filtering, which involves the application of a linear smoothing filter to lateral scan lines in an image, can reduce speckle but results in blurring of resolved structures.

Angle compounding is, at present, one of the more successful forms of averaging for speckle reduction and is based on changing the angle of incidence of the ultrasound beam on the structure to be visualized. A number of investigations based on angle compounding has been performed. The available acoustic aperture is divided into subapertures, and several images are obtained by coherently focusing within each subaperture, with the final image being formed incoherently by averaging the image set. The application of this technique is limited to regions accessible through a large field of view, and the cost for speckle reduction is some loss of lateral resolution due to subdivision of the aperture size, resulting in an increase of the lateral beamwidth.

Another approach to speckle reduction is to average several images made at different frequencies using filtering methods, frequency modulated pulses, or phase modulated pulses. However, the bandwidth of the ultrasound transducer and the frequency dependent ultrasound attenuation in tissues makes it difficult to achieve statistically independent speckle images without a loss of resolution. Further, the subdivision of the available bandwidth results in loss of axial resolution.

Accordingly, there remains a need for an ultrasound imaging system capable of effectively reducing speckle without reducing image resolution.

Various attempts have been made to improve upon the performance achieved by conventional pulse-echo ultrasound techniques. Specifically, the use of deconvolution in ultrasound has been the subject of considerable investigation. As disclosed by Fatemi et al. in "Ultrasonic B-scan imaging: Theory of image formation and a technique for restoration," *Ultrasonic Imaging,* Vol. 3, pp. 235–257 (1981), deconvolution methods based on a frequency domain Wiener filter for restoration of ultrasound B-scan images have been investigated. Further, axial deconvolution of clinical ultrasonic abdominal images with the Wiener filter have been performed, as reported by Liu et al. in "Digital processing for improvement of ultrasonic abdominal images," *IEEE Transactions on Medical Imaging,* Vol. 2, pp. 66–75 (1983).

In "Comparison of some non-adaptive deconvolution techniques for resolution enhancement of ultrasonic data," *Ultrasonics,* Vol. 27, pp. 155–164 (1989), Hayward et al. assessed a selection of deconvolution techniques for processing of ultrasound data. The greatest improvement in resolution was achieved with the L1 deconvolution method.

Since the resolution along the lateral direction is much lower than that along the axial direction, a number of attempts have been focused on deconvolution of lateral image lines. However, in "Lateral inverse filtering of ultrasonic B-scan images," *Ultrasonic Imaging,* Vol. 5, pp. 38–54 (1983), Schomberg et al. concluded that the computational effort on lateral deconvolution was wasted because of the very low resolution enhancement that could be obtained at the expense of introducing more artifacts.

Tsao et al. reported in "Reduction of sidelobe and speckle artifacts in microwave imaging: the CLEAN technique," *IEEE Transactions on Antennas and Propagation,* Vol. 36, pp. 543–556 (1988), implementation of a CLEAN algorithm for reducing sidelobe and speckle artifacts in microwave imaging. Further, in "Higher order spectra based deconvolution of ultrasound images," *IEEE Transactions on Ultrasonics, Ferroelectrics, and Frequency control,* Vol. 42, pp. 1064–1075 (1995), Aberyratne et al. investigated two dimensional deconvolution of ultrasound pulse-echo clinical images, where a 1.5–1.9 gain in axial resolution and 2.5–5.2 gain in lateral resolution was reported.

A method for determination of the acoustic impedance as a function of acoustic travel time from the reflection impulse response of the insonified tissue was originally described by Jones in "A preliminary experimental evaluation of ultrasonic impediography," *Ultrasound in Medicine,* Vol. 1, pp. 499–508 (1975). As reported by Jones et al. in "In vivo characterization of several lesions in the eye using ultrasonic impediography," *Ultrasound in Medicine, Acoustical Imaging and Holography,* Vol.8, pp.539–545 (1978), the method was applied to characterize several lesions in the eye based on recovered acoustic impedance profiles from the acquired backscattered echoes.

Beretsky, in "Raylography, a frequency domain processing technique for pulse echo ultrasonography," *Ultrasound in Medicine,* Vol. 3, p. 1581 (1977) and Papoulis et al., in "Improvement of range resolution of a pulse echo system," *Ultrasound in Medicine,* Vol.3, pp. 1613–1627 (1977), described raylography, a method which relates the reflection coefficients to the acoustic impedance of the media. The deconvolution involved frequency domain filtration of the computed transfer function for estimation of the impulse response function. Preliminary results obtained with the technique for one dimensional signals from an excised aortic wall were presented.

In "A new method of obtaining an acoustic impedance profile for characterization of tissue structures," *Ultrasound in Medicine and Biology,* Vol. 5, pp. 321–331 (1979), Herment et al. described a cross-correlation method to obtain the impulse response, for the recovery of acoustic impedance and characterized tissue structures based on their one dimensional reconstructed acoustic impedance profiles.

Both Tobocman, in "In vivo biomicroscopy with ultrasound," *Current Topics in Acoust. Res.,* Vol. 1, pp. 247–265 (1994), and Santosh et al., in "In vivo biomicroscopy with ultrasound 2," *Ultrasonics,* Vol. 28, pp. 40–49 (1990), have theoretically and experimentally demonstrated that one dimensional acoustic impedance profile reconstruction by deconvolution provides resolution improvement over the standard pulse-echo technique.

While significant research has been conducted relating to these various techniques for improving upon conventional pulse-echo technology, systems employing these techniques have not, to date, replaced conventional pulse-echo systems. To be commercially useful, any new ultrasound imaging technique must be capable of producing at least a B-scan image (i.e., a two-dimensional cross-sectional image) that is superior to those produced by existing pulse-echo systems. However, B-scan images of a tissue sample based on the acoustic impedance profile of the tissue sample have not been successfully produced. Nor has it been demonstrated that B-scan images of a tissue sample based on the acoustic impedance profile of the tissue sample would be superior to conventional pulse-echo imaging in terms of resolution, speckle and contrast.

All of the above-references articles are incorporated herein by reference in their entirety.

SUMMARY OF THE INVENTION

It is an object of the present invention to use acoustic impedance reconstruction to produce high resolution ultrasound images of biological tissue substantially free of speckle.

It is another object of the present invention to generate images that allow quantitative assessment in real time of internal injuries, growths and fractures.

It is a further object of the present invention to manufacture a portable, low-cost, ultrasound imaging system which replaces bulkier, more expensive imaging systems, such as X-ray, MRI, and CT imaging systems.

Yet another object of the present invention is to augment existing pulse-echo ultrasound B-scan systems with signal processing capabilities that produce ultrasound images based on the acoustic impedance of reflected ultrasound signals.

The aforesaid objects are achieved individually and in combination, and it is not intended that the present invention be construed as requiring two or more of the objects to be combined unless expressly required by the claims attached hereto.

According to the present invention, a compact, lightweight, low-powered diagnostic device detects, images and monitors in real time, skeletal and tissue defects and abnormalities using non-invasive ultrasound techniques. This includes such problems as cancerous nodules, fractures and imbedded foreign matter and materials undetectable by X-rays such as plastics and composites. The device is capable of monitoring bone and identifying fracture sites to determine their extent and rate of healing as well as osteoporotic condition. The device of the present invention is portable, does not require special facilities, and is capable of use in hospital examining rooms, doctors' offices and by paramedical personnel. The high resolution achieved by the present invention makes it possible to detect abnormalities and fragments as small as 0.1 mm: a resolution enhancement of a factor of five or greater compared to ultrasound imagers of conventional design.

Conventional pulse-echo medical ultrasound imaging systems display grey-scale images of cross-sectional tissue reflectivity by processing involving envelope detection (rectification and low pass filtering) or demodulation of the RF signals. The medical ultrasound imaging system of the present invention displays grey-scale images of cross-sectional tissue impedance by processing involving deconvolution of the radio-frequency (RF) signals obtained by mechanically scanning or electronically scanning (with a phased array transducer) along a line to produce a B-scan image. More particularly, the present invention involves a method for producing and displaying an image of a fundamental physical quantity: the acoustic impedance, which is obtained through a processing technique superior to envelope detection processing alone, thereby providing an image with improved spatial resolution and image quality and representing internal variations of a basic acoustic property of tissues.

Determination of the acoustic impedance involves prefiltering of the incident RF ultrasound signal sequence and the RF ultrasound signal sequence reflected from the specimen to be imaged. Specifically, a time domain window function, such as a Hamming window, is applied to both the incident and reflected ultrasound sequences. Prefiltering minimizes the effects of spectral leakage caused by the Fast Fourier transform (FFT) calculation of a finite time sequence. An N-point real FFT is computed for both the digitized incident and reflected signals to obtain the incident and reflected spectrums, and a complex division of the reflected spectrum by the incident spectrum is performed to obtain the transfer function.

An important aspect of the present invention is the application of a window function to the transfer function prior to performing an inverse FFT to obtain the impulse response. It has been found by the present inventors that conventional filtering, which reduces the amplitude of high and low frequencies of the transfer function frequency components with a window that smoothly approaches zero at the high and low frequencies, produces a relatively poor acoustic impedance profile. According to the present invention, a window function is applied to the complex transfer function array with a sharp cutoff at the low frequency end of the spectrum, i.e., below a certain frequency component, the amplitude of the frequency components is set to zero, while the amplitude of the certain frequency component and those higher are not reduced. For example, the low cutoff can be placed at the first, second or third frequency point after the DC term in the transfer function array. The high cutoff of the window is placed at the frequency point corresponding to the high cutoff bandwidth of the transducer. At the high frequency end, the window function can have a sharp cutoff or can smoothly approach zero to gradually attenuate the frequency component amplitudes at the high frequency end.

Optionally, the values of the low frequency transfer function amplitudes are assigned by constraints imposed on the impedance profile by prior knowledge in order to correct poorly determined low frequency amplitudes resulting from the limited bandwidth of the transducer. Further, each windowed transfer function may be multiplied by an exponential factor to compensate for the frequency-dependent attenuation caused by an intervening tissue layer.

An inverse FFT of the windowed transfer function array is computed to obtain the estimated impulse response array.

The acoustic impedance of individual A-scans is calculated from the impulse response using the plane wave Born approximation. By mechanically or electronically scanning the transducer along a line, a series of A-scan acoustic impedance profiles are calculated and used to produce a two-dimensional B-scan image. The transducer can be a phased array of small sensors mounted in a stowable thin flexible pad to perform the real time, large sector scanning needed for rapid acquisition of information.

The sharp, low-frequency cutoff of the window function of the present invention produces an acoustic impedance profile which is virtually free of speckle and which has a higher resolution than conventional pulse-echo systems. This is an unexpected result, since it is well known in the art that a sharp cutoff in the frequency domain produces oscillations or ringing in the time domain and generally degrades images generated from the pulse-echo signal or the impulse response.

It has further been found that, due to the importance of the low frequency characteristics of the transducer in determining the large-scale behavior of the acoustic impedance, the acoustic impedance image quality increases with decreasing transducer frequency, provided that the transducer bandwidth is sufficient to adequately represent the intermediate frequency reflectivity characteristics of the specimen being imaged. This also is an unexpected result, since it is well known in the art that, all else being equal, resolution increases with higher frequency. The relatively low center frequency (3 MHz to 5 MHz for an 8 mm field of view) of the transducer of the present invention provides greater depth penetration with image quality and resolution exceeding those of conventional pulse-echo systems operating at higher frequencies. In fact, it has been demonstrated by the present inventors that images generated using acoustic impedance reconstruction with a 3.5 MHz transducer are superior to pulse-echo images generated with a 20 MHz transducer in terms of resolution, contrast and speckle characteristics.

Additionally, the present invention advantageously combines imaging in a small field of view with a low center frequency transducer, so that a good depth of penetration for visualization of deeper structures is achieved, while superior spatial depth resolution than is currently obtained through higher frequency transducers is maintained.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

BRIEF DESCRIPTION OF THE DRAWINGS

FIGS. 1a and 1b is a functional block diagram illustrating the processing steps for calculation the acoustic impedance response, including an iterative process for setting the amplitudes of the low frequency components of the transfer function.

FIGS. 4a–4c respectively illustrate the pulse-echo, impulse response, and acoustic impedance B-scan images from an aluminum block phantom.

FIGS. 5a–5c respectively illustrate the pulse-echo, impulse response, and acoustic impedance B-scan images from a plastic phantom.

FIGS. 11a–11c respectively illustrate the pulse-echo, impulse response, and acoustic impedance B-scan images from an in vitro colon specimen obtained with a 20 MHz transducer.

FIGS. 16a and 16b respectively illustrate the pulse-echo B-scan images of two pig artery specimens generated with a 3.5 MHz transducer, and FIGS. 16c and 16d respectively illustrate the corresponding acoustic impedance B-scan images.

FIGS. 17a and 17b respectively illustrate the pulse-echo B-scan images of two additional pig artery specimens generated with a 3.5 MHz transducer, and FIGS. 17c and 17d respectively illustrate the corresponding acoustic impedance B-scan images.

FIGS. 19a–19d respectively illustrate, for a field of view corresponding to 1024 depth sample points, the pulse-echo B-scan image of a plastic phantom and the corresponding acoustic impedance B-scan images with three different rectangular window functions.

FIGS. 20a–20d respectively illustrate, for a field of view corresponding to 2048 depth sample points, the pulse-echo B-scan image of a plastic phantom and the corresponding acoustic impedance B-scan images with three different rectangular window functions.

FIGS. 22a–22c respectively illustrate a pulse-echo B-scan image of a pig artery specimen sampled with a 12 bit digiter, the acoustic impedance B-scan image of the pig artery obtained without prefiltering of the pulse-echo signal, and the acoustic impedance B-scan image of the pig artery obtained with prefiltering of the pulse-echo signal.

FIGS. 23a–23c respectively illustrate a pulse-echo B-scan image of a pig artery specimen sampled with an 8 bit digiter, the acoustic impedance B-scan image of the pig artery obtained without prefiltering of the pulse-echo signal, and the acoustic impedance B-scan image of the pig artery obtained with prefiltering of the pulse-echo signal.

FIGS. 24a–24c respectively illustrate the pulse-echo B-scan images of a plastic phantom using 3.5, 5 and 20 MHz transducers. FIGS. 24d–24f respectively illustrate the acoustic impedance B-scan images of the phantom using the 3.5, 5 and 20 MHz transducers.

FIGS. 25a and 25b respectively illustrate the pulse-echo B-scan image of a plastic phantom generated from a 3.5 MHz transducer and a 20 MHz transducer.

FIGS. 26a and 26b respectively illustrate the pulse-echo B-scan image of the plastic phantom from the 20 MHz transducer and the acoustic impedance B-scan image of the plastic phantom generated from a 3.5 MHz transducer.

DETAILED DESCRIPTION OF THE PREFERRED EMBODIMENTS

Specific acoustic impedance is an acoustic parameter, analogous to electrical impedance, and is defined as the ratio of the pressure amplitude to the velocity. In general, this is a complex quantity dependent on the relative phase of the pressure and velocity which in turn may be dependent on the type of the wavefield and the propagating conditions. A distinct parameter is the characteristic acoustic impedance which is a property of the medium and is equal to the specific acoustic impedance only for the case of plane wave propagation in a medium.

The term acoustic impedance as used herein refers to the characteristic acoustic impedance which is the product of the medium density $\rho$ and the speed of sound c in the medium:

$$Z = \rho c \tag{6}$$

Figure 1:
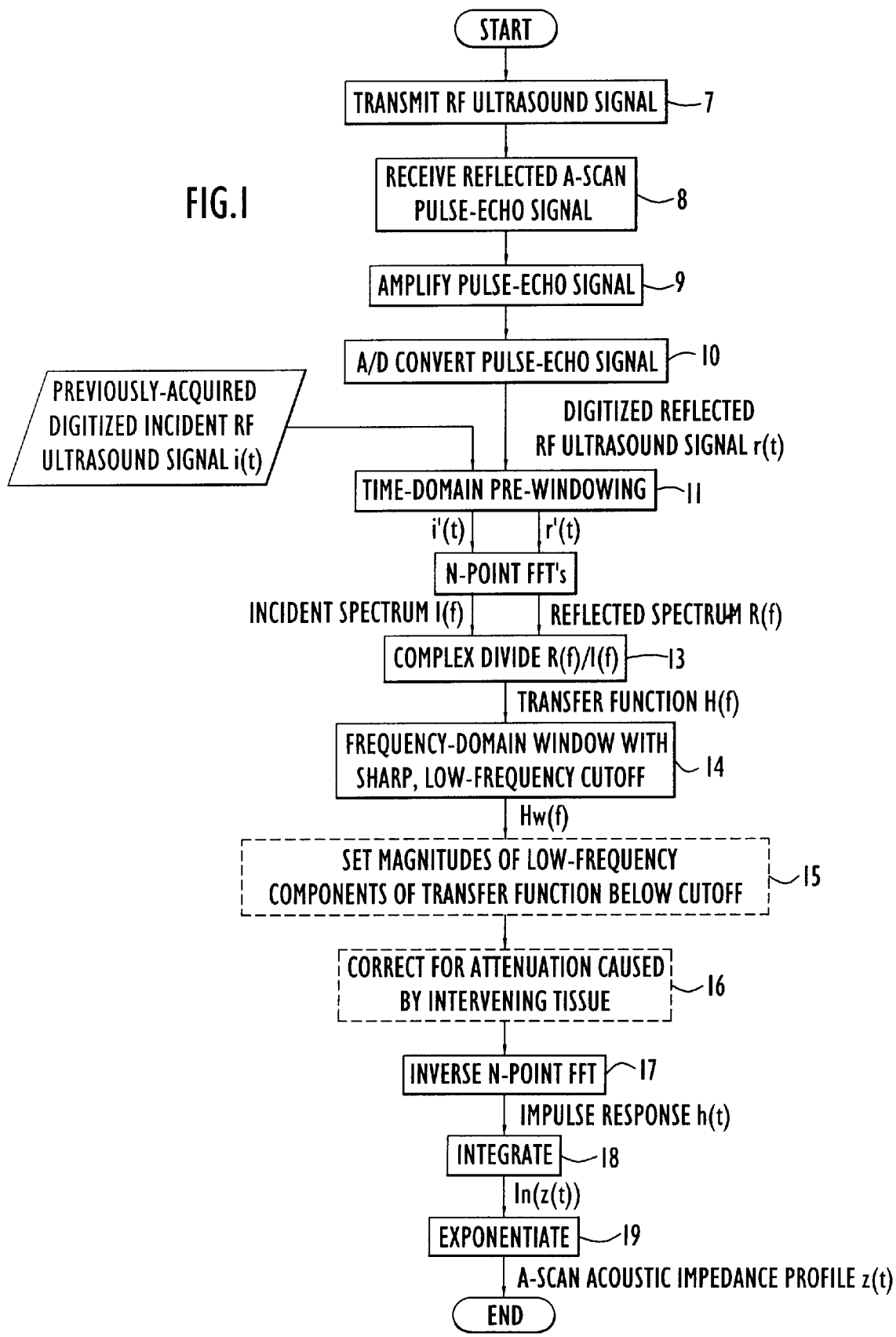
FIG. 1 is a functional block diagram illustrating the processing steps for calculation of the acoustic impedance response according to an exemplary embodiment of the present invention.
Figure 1B:
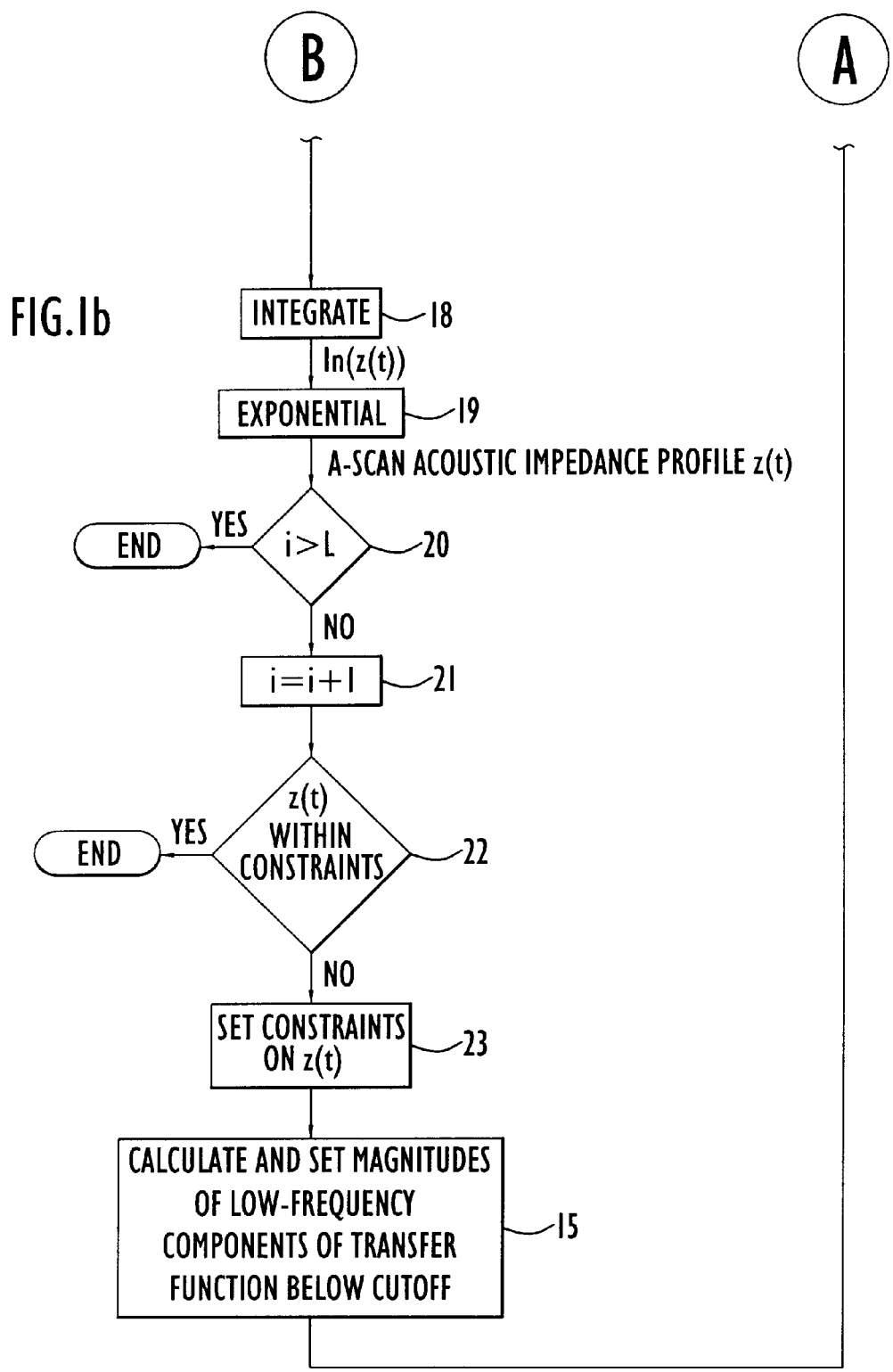

The determination of the acoustic impedance from the reflectivity profile requires: 1) acquisition of the reflectivity profile signal r(t) from the medium and the incident ultrasonic wave i(t); 2) processing of the reflectivity profile by deconvolution to obtain the impulse response h(t); and 3)

determination of the acoustic impedance profile z(x) from the impulse response h(t). FIG. 1 is a functional block diagram illustrating the processing steps for calculation of the acoustic impedance response along a path traveled by an ultrasonic pulse, according to a preferred embodiment of the present invention.

In step 7, an incident RF ultrasound pulse is transmitted by a transducer toward a target to be imaged. The incident pulse travels along a substantially linear path through the target, and at least a portion of the energy of the pulse is reflected back toward the transducer as the pulse interacts with the target. The reflected A-scan pulse-echo signal is received by the transducer (step 8), amplified (step 9), and converted to a digital signal r(t) by an analog-to-digital (A/D) converter (step 10).

The next step in determining the acoustic impedance profile involves pre-windowing of the digitized incident RF ultrasound signal sequence i(t) and the RF ultrasound signal sequence r(t) reflected from a specimen. As explained in greater detail hereinbelow, the incident ultrasound profile i(t) can be determined from acquisition of the reflection profile from an aluminum block or the like placed at the focal length of the transducer and inversion of the digitized signal in time. In accordance with step 11, a time domain window function, such as a Hamming window, is applied to both the ultrasound reflection r(t) and incident i(t) sequences. This forces the amplitude of the time sequences at both the beginning and the end of the sample interval to go smoothly toward a single common amplitude value. Pre-windowing minimizes the effects of spectral leakage caused by the Fast Fourier transform (FFT) calculation of a finite time sequence.

An important aspect of the present invention is size of the field of view in the depth dimension provided by the incident/reflected pulse. It has been determined that, by decreasing the field of view in the depth dimension, the quality of the resulting acoustic impedance image can be improved. The field of view can be controlled via the digital sampling of the incident i(t) and reflected r(t) pulse signals. For a given sampling rate, the number of sample points taken determines the extent of the field of view in the depth dimension. Thus, provided the features to be imaged are contained within the field of view, it is preferable to take fewer samples at a given sampling rate (e.g., taking 512 sample points is preferable to taking 1024 sample points, which is preferable to taking 2048 sample points). Advantageously, the smaller number of samples also reduces the computational burden associated with calculating the FFT and inverse FFT required to determined the acoustic impedance.

In practice, the field of view is chosen to be sightly larger than the size of the tissue structure to be imaged. The theoretically ideal field of view is one half the wavelength of the lowest frequency sound that contributes substantially to the incident pulse; however, this is much too small to be practical.

In the presence of no noise, the reflected signal r(t) is a convolution of the incident signal i(t) with the tissue impulse response h(t):

$$r(t) = h(t) \otimes i(t) \quad (7)$$

Hence, the system transfer function is given by:

$$H(f) = \frac{R(f)}{I(f)} \quad (8)$$

As shown in FIG. 1, in step 12, the reflected spectrum R(f) and incident spectrum I(f) are respectively obtained by computing an N-point real FFT of the windowed reflected RF signal r(t) (the amplified and digitized ultrasound reflection from the specimen) and the windowed incident signal i(t) (the digitized echo from a strongly reflecting target such as an aluminum block), where N is the number of sample points that have been digitized (e.g., 512, 1024, 2048). In step 13, the transfer function H(f) is obtained by performing a complex division of the reflected spectrum R(f) by the incident spectrum I(f).

In principle, the system impulse response h(t) can be determined exactly from an inverse Fourier transformation of equation 8. However, due to the presence of noise and the finite bandwidth of the transducer, the computed spectrum H(f) is unreliable outside the bandwidth ($f_1$, $f_2$) of I(f). To reduce the resulting error, the computed spectrum H(f) is multiplied by a window function W(f) that attenuates the frequency components outside ($f_1$, $f_2$):

$$H_w(f) = H(f)W(f) \quad (9)$$

When determining the impulse response from the transfer function, the window function conventionally applied to the transfer function H(f) is a filter that smoothly approaches zero amplitude at high and low frequencies. However, it has been determined by the present inventors that this conventional windowing approach produces a relatively poor acoustic impedance profile.

It has been discovered by the present inventors that a window function with a sharp cutoff at the low frequency end produces superior acoustic impedance images. Accordingly, in step 14, a frequency domain window function W(f) is applied to the magnitude of the complex transfer function array with a sharp cutoff at the low-frequency end of the window. That is, the magnitudes of the frequency components of the transfer function below a certain frequency component are set to zero, while the magnitudes of the certain frequency component and higher frequency components are not attenuated. The phases of the frequency components in the complex transfer function array are not changed.

At the high frequency end of the window, a sharp cutoff can be placed at the frequency component corresponding to the high cutoff bandwidth of the transducer used to image the specimen. In this case, the window function is rectangular, having sharp high and low frequency cutoffs, with the magnitudes of the frequency components outside the window being set to zero and the magnitudes of the frequency components within the window being unattenuated. Alternatively, at the high frequency end, the window function can be a filter which smoothly approach zero amplitude to gradually increase attenuation of the high frequency components of the transfer function with increasing frequency. For example, a window that does not have a sharp transition region, such as Hamming, Hanning, Blackman, etc., can be applied at the high frequency end.

It has been found by the present inventors that the sharp, low-frequency cutoff of the window function of the present invention produces an acoustic impedance profile which is virtually free of speckle and which has a higher resolution than conventional pulse-echo systems. This is an unexpected result, since it is well known in the art that a sharp cutoff as in the frequency domain produces oscillations or ringing in the time domain and generally degrades images generated from the pulse-echo signal or the impulse response.

The unexpectedly superior performance of the sharp, low-frequency cutoff window function may be explained by the important role of the low frequency characteristics of the transducer, which was heretofore not fully appreciated. The overall shape or large-scale features of the acoustic impedance profile (i.e., the amplitude profile of the acoustic impedance as a function of depth along a line in the depth dimension for a single A-scan) is determined by the low frequency components of the transfer function used to calculate the acoustic impedance profile. It is important to preserve the large-scale features of the acoustic impedance in order to produce an image that presents the intermediate frequency (1 MHz to 8 MHz) information, which represents the image features of medical interest, in a readable manner. The low frequency components of the transfer function, in turn, are determined by the spectrum of the incident ultrasound signal I(f) and the spectrum of the reflected ultrasound signal R(f). However, due to the finite bandwidth of the transducer, the low frequency components of the transfer function can be unreliable and tend to corrupt the resulting acoustic impedance profile. Thus, a conflict exists between the need to preserve the low frequency components of the transfer function in order to obtain the overall shape of the A-scan impedance profile, and the need to eliminate the degradation to the acoustic impedance profile caused by corruption of the low frequency components of the transfer function resulting from the finite bandwidth of the transducer.

It has been found by the present inventors that a sharp, low-frequency cutoff achieves a desirable tradeoff between retention of low frequency characteristics and elimination of corruption from unreliable low-frequency components of the transfer function. Further, the sharp cutoff does not introduce unacceptable oscillations or ringing in the resulting acoustic impedance image. The optimal placement of the low-frequency cut-off is a function of the transducer's low frequency characteristics, with better low-frequency characteristics allowing the cutoff to be placed at a lower frequency component. For example, for a transducer with excellent low-frequency characteristics (e.g., significant energy being radiated between 100 and 1000 kHz), the low-frequency cutoff can be placed as low as the first frequency component after the DC term (the lowest frequency component) in the transfer function array (i.e., with the lowest frequency component and higher components remaining unattenuated). For transducers having poorer low frequency characteristics, the low-frequency cutoff can be placed at the second, third, fourth, etc., lowest frequency component after the DC term in the transfer function array. The magnitude of the DC component is always set to zero. The negative frequency components are the complex conjugates of the positive frequency components.

It has further been found that the Born approximation inverse scattering method of capturing the acoustic impedance produces images having greater resolution by a factor of approximately five as compared to images of the reflectivity produced by the conventional pulse-echo method. The improvement in resolution can be understood in the following way. The pulse-echo method ignores the wave nature of ultrasound. It regards the incident pulse as a localized field of energy. Thus, in the pulse-echo method, a structure must be larger than the pulse length to be resolved; the pulse length can be no smaller than a wavelength (of the dominant frequency) or two. In contrast, the inverse scattering technique of the present invention recognizes that the ultrasound pulse is a wave field and so, in principle, is capable of resolving structures as small as a quarter wavelength.

The enhanced resolution achieved by the system of the present invention permits the use of lower frequency ultrasound. The relatively low operating frequencies which can be used with the system of the present invention provide greater depth penetration with image quality and resolution exceeding that of conventional pulse-echo systems operating at higher frequencies. For example, at a transducer center frequency of approximately 5 MHz, spatial resolution on the order of 0.1 mm is achievable in the depth dimension.

Importantly, most of the image information representing anatomic structures of interest is contained in the intermediate frequencies (i.e., frequencies between 1 MHz and 8 MHz) present in the reflected ultrasound pulses, due to the inherent acoustic impedance properties of anatomic structures. For example, while frequencies below 1 MHz generally define the overall shape of the acoustic impedance profile, they do not contribute significantly to forming the finer details of medical interest in the resulting image. Likewise, frequencies above 8 MHz are not required to resolve most anatomical structures of interest using acoustic impedance. Transducers having center frequencies in the range between 3 MHz and 5 MHz generally transmit sufficient low-frequency (<1 MHz) energy to preserve the large-scale shape of the acoustic impedance profile, while having a center frequency and bandwidth that are well matched to the intermediate frequencies corresponding to image features of interest. Of course, transducers with any center frequency can be employed in the system of the present invention provided that the low and intermediate frequency characteristics of the transducer are adequate to reconstruct the acoustic impedance profile.

Prior to computing an estimate of the impulse response h(t) from the windowed transfer function $H_w(f)$, two optional processing steps may be performed. Specifically, in optional step 15, the values of the amplitudes of the low-frequency components of the transfer function can be assigned by constraints imposed on the impedance profile by prior knowledge. In this case, it is assumed that at least one of the frequency components of the transfer function above the DC term is unreliable due to the limited bandwidth of the transducer. Accordingly, the low-frequency cutoff of the window function is set above the unreliable low-frequency component(s) of the transfer function such that the magnitude of the low-frequency component(s) is set to zero. The magnitude of the low-frequency component(s) below the cutoff is then set in accordance with the constraints applied in step 15.

For example, although the amplitude of the acoustic impedance profile theoretically should never be less than 1.0 in lean tissue, an absence of low frequency information in the transfer function can cause the computed acoustic impedance to be less than 1.0 at points in the A-scan profile. Thus, one constraint applied in step 15 can be the requirement that the amplitude of computed acoustic impedance profile be no less than 1.0. Constraints imposed on the value of the acoustic impedance at certain depths in the profile can then be used to determine the magnitude of the low-frequency components of the transfer function.

Although these low-frequency constraints alter the large-scale features (i.e., the overall shape) of the acoustic impedance profile, they do not significantly affect the finer features of the profile which are represented in the intermediate frequency components of the transfer function and which contain the image details of medical interest. A method for setting constraints and determining the low-frequency components of the transfer function therefrom is described below in detail.

In optional step 16, the frequency-dependent attenuation caused by an intervening tissue layer is compensated for by multiplying each windowed transfer function magnitude by an exponential factor. For example, if it is assumed that the attenuation coefficient of the intervening tissue layer is linear in the wave number, $u(k)=\beta k$, where k is the wave number, the components of the transfer function are then corrected for the attenuation caused by the intervening tissue layer in accordance with the following expression:

$$H(k)=H(k)\exp(2\beta dk)$$

where d is the thickness of the intervening tissue layer. Thus, the correction is dependent on the single parameter $\beta d$, which can be determined by trial and error.

An estimate of the impulse response array h(t) is obtained in step 17 by computing an inverse FFT of the windowed transfer function array $H_w(f)$ (which optionally has been further processed in steps 15 and 16). The imaginary components of the terms in the impulse response array h(t) are considered to be computational errors and are disregarded; thus, the estimated impulse response h(t) is a real array.

In steps 18 and 19, the acoustic impedance z(x) is calculated from the impulse response h(x), using the plane wave Born approximation, by integrating the impulse response array h(x) and by exponentiating the result in accordance with the following relationship:

$$z(x) = \exp 2 \int_0^{2x} h(x) dx \qquad (10)$$

This relationship between the impulse response and acoustic impedance is derived as follows. The propagation of the ultrasound wave in a medium is governed by the following one-dimensional differential wave equation:

$$\frac{d^2 \psi_k(x)}{dx^2} + k^2 \psi_k(x) = \left(\frac{d}{dx}\ln z(x)\right)\frac{d\psi_k(x)}{dx} \qquad (11)$$

where, $\psi_k$ is the excess pressure wavefield, x is the elapsed travel time multiplied by the speed of sound in water, z is the relative (to water) acoustic impedance of the tissue, and $$k = \frac{2\pi f}{c} \text{ is the wavenumber.}$$

is the wavenumber.

The ultrasound pulse initially travels a distance of $L_1$ in a water medium with a relative acoustic impedance of unity before interacting with the scattering layer in which the acoustic impedance is unknown. The starting travel point for x is taken to be the point where the ultrasound pulse is emitted from the source (see FIG. 2).

Figure 2:
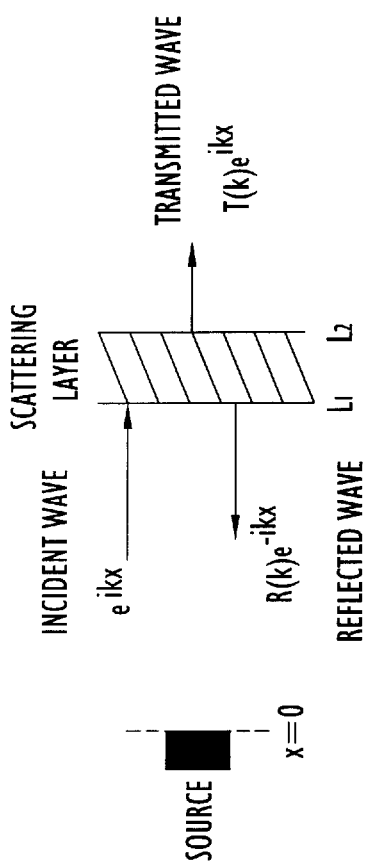
FIG. 2 is a schematic illustration of an incident wave from a source and the corresponding reflected and transmitted waves from a layered medium.

In accordance with the arrangement shown in FIG. 2, the boundary conditions are defined as follows:
For $x<L_1$, $$\psi_k(x)=e^{ikx}-R(k)e^{-ikx} \qquad (12)$$

For $x>L_2$, where $L_2=L_1+\Delta L$, and $\Delta L$ is the thickness of the tissue layer, $$\psi_k(x)=T(k)e^{ikx} \qquad (13)$$

where R(k) and T(k) are reflection and transmission coefficients of the reflected and transmitted wavefields respectively. For simplicity, the time dependent phase factor $e^{-ikct}$ has not been shown in equations 12 and 13.

The formal solution of the differential wave equation (equation 11) is given by:

$$\Psi_k(x) = e^{ikx} + \frac{1}{2ik}\int_{L_1}^{L_2} e^{ik|x-x'|}\left(\frac{d}{dx'}\ln z(x')\right)\frac{d}{dx'}\psi_k(x')dx' \qquad (14)$$

Given the boundary condition of equation 12, for $x<L_1$, $$\psi_k(x)=e^{ikx}-R(k)e^{-ikx} \qquad (15)$$

Comparing equations 14 and 15, it is seen that for $x<L_1$, $$R(k) = -\frac{1}{2ik}\int_{L_1}^{L_2} e^{ikx'}\left(\frac{d}{dx'}\ln z(x')\right)\frac{d}{dx'}\psi_k(x')dx' \qquad (16)$$

Equation 16 is the solution of the direct scattering problem for the reflection coefficient. Given the acoustic impedance profile and the incident wave, equation 16 can be used to solve for the reflection coefficients.

Under the assumption that the variations in the acoustic impedance of tissue are small, and the speed of sound in tissue is approximately constant, the wavefield inside the tissue in equation 16, $\psi_k Pk(X)$, can be set equal to the incident source wave $e^{ikx}$ which is the plane wave Born approximation (PWBA) given by:

$$\psi_k(x') \approx e^{ikx'} \qquad (17)$$

Substitution of equation 17 in equation 16 yields:

$$R(k) \approx -\frac{1}{2}\int_{L_1}^{L_2} e^{2ikx}\frac{d}{dx'}\ln z(x) dx \qquad (18)$$

The reflection amplitude R(k) is the Fourier transform of the impulse response.

The incident wave emitted by the source is a pulse and the incident wavefield can be represented by a Fourier integral. The incident pulse can thus be represented as:

$$\Psi_{inc}(x) = \int_0^{+\infty} \{A(k)e^{ikx} + A(k)^* e^{-ikx}\} dk \qquad (19)$$

where A(k) is the Fourier transform of the incident pulse. The reflected pulse can be represented as:

$$\Psi_{ref}(x) = -\int_0^{+\infty} \{R(k)A(k)e^{-ikx} + R(k)^*A(k)^* e^{ikx}\} dk \qquad (20)$$

where $-R(k)^*A(k)^*$ is the Fourier transform of the reflected pulse, $$\psi_{ref}(k)=-R(k)^*A(k)^* \qquad (21)$$

A(k) is the Fourier transform of the incident pulse, $$\Psi_{inc}(k) = A(k) \quad (22)$$

The ratio of equation 21 by equation 22 yields, $$R(k) = -\frac{\Psi_{ref}(k)^*}{\Psi_{inc}(k)} \quad (23)$$

The impulse response wavefield is the inverse Fourier transform of the reflection coefficient, R(k), and is theoretically obtained by evaluating equation 20 for the case where the incident wave is a delta function, $\psi_{inc}(t) = \delta(t)$, $$\Psi_{ir}(x) = -\frac{1}{2\pi}\int_0^{+\infty} \{R(k)e^{-ikx} + R(k)^* e^{ikx}\} dk \quad (24)$$

Substitution in equation 24 of the expression given for the amplitude R(k) in equation 18 yields the final equation which relates the acoustic impedance to the impulse response:

$$z(x) = \exp 2\int_0^{2x} \Psi_{ir}(x) dx \quad (10)$$

Thus, the acoustic impedance profile z(x) can be obtained by integrating and exponentiating the estimated impulse response h(t) in accordance with equation 10. It should be noted that two different arguments x and t are used with the acoustic impedance profile z throughout the description of the invention. It will be understood that z(x) and z(t) are one and the same profile, although the argument x is generally used where the profile z is described in the context of the spacial depth dimension, while the argument t is generally used where the profile z is described in the context of time.

It has been observed by the present inventors that the primary consequence of ignoring the contribution of the lowest frequency transfer function amplitudes (i.e., by applying a sharp, low-frequency cutoff which sets to zero the amplitude of at least one component of the transfer function above the DC term) is that the A-scan impedance profile z(t) as a whole tends to "sag" so that its magnitude falls below the value of 1.0 in some regions. The "sag" can be rectified by constraining a number of low lying points (e.g., local minima) in the profile to have a value of 1.0 or greater. That is, as explained above with respect to step 15, the values of the magnitudes of the low-frequency components of the transfer function below the low-frequency cutoff can be calculated from the constraints imposed on the acoustic impedance profile z(t).

A method for setting the magnitudes of the low-frequency components of the transfer function below the low-frequency cutoff will now be described in conjunction with the flow diagram illustrated in FIG. 1a. The method of setting the low-frequency components shown in FIG. 1a is an iterative process. In step 14, the low-frequency-cutoff window function is applied to the transfer function. In this case, the cutoff is located such that at least one frequency component above the DC term has its amplitude set to zero. In step 14a, an iteration counter i is set to 1. In the initial iteration, since no constraints have yet been imposed on z(t), the amplitudes of the low-frequency components remain set to zero, and step 15 is not performed. Steps 16–19 are then performed in accordance with the foregoing description to determine the acoustic impedance profile z(t).

In step 20, it is determined whether iteration counter i is greater than the maximum number of iterations L. If so, the processing for the A-scan profile is concluded, with the computed impedance profile z(t) being retained and displayed and/or stored in a memory, as described below, and the next A-scan is then begun (a sequence of adjacent A-scans is performed in order to generate a B-scan image). Note that if the maximum number of iterations L is set to 0, the amplitudes of the low-frequency components below the low-frequency cutoff are not computed and remain zero, i.e., optional step 15 is not performed.

If the iteration counter is not greater than the maximum number of iterations L, the iteration counter i is incremented by 1 (step 22). The acoustic impedance profile z(t) is then analyzed to determine whether it meets certain criteria. For example, it can be determined in step 22 whether the acoustic impedance z(t) remains at or above 1.0 over the entire profile. If the acoustic impedance profile meets the criteria, the processing for the A-scan profile is concluded, with the most recently computed impedance profile z(t) being retained and displayed and/or stored in a memory, as described below. The next A-scan for the B-scan image is then begun.

If the acoustic impedance profile does not meet the criteria assessed in step 22, constraints are placed on the acoustic impedance profile z(t) in step 23. In particular, the acoustic impedance profile z(t) is divided into N regions, where N is an integer greater than 1. For example, the profile z(t) can be divided into 5 or 6 equal regions. In each region n, if the profile falls below 1.0, the minimum profile point Zmin(tn) for that region is determined, and $z(t_n)$ is constrained to have a value of 1.0. In general, this process will yield a set of constraints for the acoustic impedance profile: $t_1, z(t_1); t_2, z(t_2); \ldots ; t_N, Z(t_N)$.

In step 15, the constraints imposed on the acoustic impedance profile in step 23 are used to determine the values of the low-frequency components of the transfer function H(ω) below the low-frequency cutoff by relating the acoustic impedance z(t) to the to the transfer function H(ω). Specifically, the impulse response I(t) is given by:

$$I(t) = \frac{1}{2\pi}\int e^{i\omega t} d\omega H(\omega) \quad (25)$$

$$\ln z(t) = 2\int_0^{2t} dt' I(t') = \frac{1}{\pi}\int d\omega H(\omega) \int_0^{2t} dt' e^{i\omega t'} \quad (26)$$

$$= \int d\omega H(\omega)\frac{1}{\pi}\frac{(e^{i2\omega t}-1)}{i\omega} = \int d\omega H(\omega)\frac{2}{\pi\omega}e^{i\omega t}\sin\omega t \quad (27)$$

$$= \int d\omega H(\omega)J(\omega, t) \text{ where } J(\omega, t) = \frac{2}{\pi\omega}e^{i\omega t}\sin\omega t \quad (28)$$

For numerical evaluation on a computer the integral in equation 28 is approximated by a discrete sum:

$$\ln z(t_n) = \sum_{m=1}^M \Delta\omega J(m\Delta\omega, t_n) H(m\Delta\omega) \quad (29)$$

where Δω is small and m is large, and n=1, ..., N, where N is the number of constraints imposed on the acoustic impedance profile, i.e.; $t_1, z(t_1); \ldots ; t_n, z(t_n)$. Simplifying the station, equation 29 reads:

$$Z_n = \sum_{m=1}^{M} J_{nm} H_m \qquad (30)$$

where $Z_n = \ln z(t_n)$, $H_m = H(m\Delta\omega)$, and $J_{nm} = \Delta\omega J(m\Delta\omega, t_n)$.

Given that the low-frequency cut-off frequency of the window function applied in step 14 is $\omega_0$ let $\omega_0 \approx k\Delta\omega$, and let the high-frequency cutoff of the window function equal $M\Delta\omega$. Then equation 30 can be rewritten to read:

$$Z_n = \sum_{m=1}^{k} J_{nm} H_m + \sum_{m=k+1}^{M} J_{nm} H_m \qquad (31)$$

It is the values of $H_m$ in the first sum on the left in equation 31 that are to be determined by the constraints imposed on the acoustic impedance profile. The values that appear in the second sum correspond to $H(\omega)$ for $\omega > \omega_0$, i.e., the frequency components of the transfer function $H(\omega)$ that are above the low-frequency cutoff and whose measured values are considered reliable. Accordingly, let:

$$\tilde{Z}_n = Z_n - \tilde{H}_n = Z_n - \sum_{m=k+1}^{M} J_{nm} H_m = \sum_{m=1}^{k} J_{nm} H_m \qquad (32)$$

There are N equations (n=1, ..., N) in the form of equation 32, one for each constraint $z(t_n)$, which can be used to solve for k unknowns (m≤k), i.e., the k frequency components of $H_m$ below the low-frequency cutoff. In the case where k=N, J would be a square matrix and could be inverted, $$H_m = \sum_{n=1}^{N} (J^{-1})_{mn} \tilde{Z}_n \qquad (33)$$

In general, N<k so the problem is under-determined. Then, in accordance with inverse theory, the solution of least norm is $$H_m = \sum_{n=1}^{N} (J^t(JJ^t)^{-1})_{mn} \tilde{Z}_n \qquad m = 1, 2, \ldots, k \qquad (34)$$

where $J^t$ is the Hermitian conjugate of J.

From equation 34, the k low frequency components of the transfer function $H(\omega)$ below the low frequency cutoff ($\omega < \omega_0$) can be calculated from the specified constraint values $t_1, z(t_1); t_2, z(t_2); \ldots ; t_N, z(t_N)$.

Once the amplitudes of the low-frequency components of the transfer function are calculated in step 15 in accordance with equation 34, processing returns to step 16, and the acoustic impedance profile is recalculated using the calculated amplitudes of the low-frequency components of the transfer function. As shown in FIG. 1a, the processing steps for recomputing the acoustic impedance and recalculating the amplitudes of the low frequency components of the transfer function are repeated until the number of iterations exceeds the maximum number of iterations L (step 20) or until the acoustic impedance profile meets the criteria assessed in step 22.

The above described process of reconstructing the acoustic impedance employs the plane wave Born approximation, and yields exceptionally good results in terms of image resolution, contrast, and speckle. However, it will be understood that other inverse scattering methods, such as an iterative inverse scattering method, may be employed within the system of the present invention.

The acoustic impedance profile calculated in accordance with the process shown in FIG. 1 (or FIG. 1a) is an A-scan profile which comprises a plot of the amplitude of the acoustic impedance as a function of depth along a line extending in the depth direction (i.e., the line along which the incident/reflected pulse traveled). In accordance with the present invention, a series of adjacent A-scan acoustic impedance profiles are generated as the transducer scans a section of a tissue sample. That is, the transducer is either mechanically displaced along a line lying in a plane substantially perpendicular to the direction in which a sequence of pulses is emitted or the transducer is a phased array of elements which can be electronically controlled to emit a sequence of pulses in a plurality of different directions, wherein each pulse is a composite pulse whose direction is controlled by the relative phases of the individual transducer elements.

The series of adjacent A-scan acoustic impedance profiles are used to generate a single, two-dimensional B-scan image. Specifically, the B-scan image represents a planar cross-section of the specimen in the depth dimension (abscissa) and the lateral dimension (ordinate). Each A-scan profile forms a column of pixels in the B-scan image such that the sequence of adjacent A-scans forms side-by-side columns of pixels in the B-scan image, with the amplitude of the acoustic impedance being represented in grey-scale. The digital image, which can be stored in a conventional memory device, can be generated on any conventional imaging device, including, but not limited to, a cathode ray tube, a liquid crystal display, a printer, or film.

Another unexpected result achieved with the method of the present invention is the virtual elimination of speckle from the resulting acoustic impedance B-scan image, as shown in the experimental results hereinbelow. In contrast to known techniques for eliminating speckle, the process of the present invention eliminates speckle without sacrificing spatial depth resolution. The fact that the images produced by the inverse scattering technique of the present invention are free of the speckle that corrupts the pulse-echo method images is a consequence of the fact that these images are pictures of the acoustic impedance distribution, whereas the pulse-echo method provides an image of the reflectivity distribution. The interiors of the artery wall specimens which were studied are relatively homogeneous, and the reflectivity is negligibly small inside the artery wall. Thus, the coherent background noise appears very clearly as speckle. The impedance inside the artery wall is greater than the impedance of the surrounding water by a considerable amount so that the B-scan image of the artery wall in the grey-scale plot is a bright ribbon. The small variations in impedance contributed by coherent background noise have small visual impact when added to the bright ribbon image of the acoustic impedance of the artery wall.

The processing required to calculate and display the acoustic impedance B-scan image can be performed in real time by a typical personal computer; thus, the acoustic impedance image generation of the present invention can be performed using conventional system components including: the transducer, the scanning mechanism, the hardware for pulse generation and front-end signal processing of pulse reflections, the display mechanism, and the system controller. In particular, the scanning rate can be that used with a conventional pulse-echo imaging system. Consequently, the process of the present invention can be implemented in existing pulse-echo systems without additional hardware simply by augmenting the signal processing performed in accordance with the step shown in FIG. 1 (or FIG. 1a). Moreover, real time processing allows the displayed image to be continually updated in real time to simulate a moving image. The process of the present invention can also be implemented in a portable, light-weight, low-power system, as described hereinbelow.

While the acoustic impedance technique of the present invention is described herein in the context of B-scan imaging, it will be understood that process of the present invention can be applied to other types of imaging, including three-dimensional images such as those generated from multiple linear scans.

The present inventors have experimentally verified that the image quality of the acoustic impedance B-scan images obtained in accordance with the above-described process is superior to that found in conventional pulse-echo B-scan images in terms of resolution, contrast and speckle. Specifically, the results of a series of experiments described hereinbelow demonstrates the performance and advantages of the imaging system of the present invention.

Figure 3:
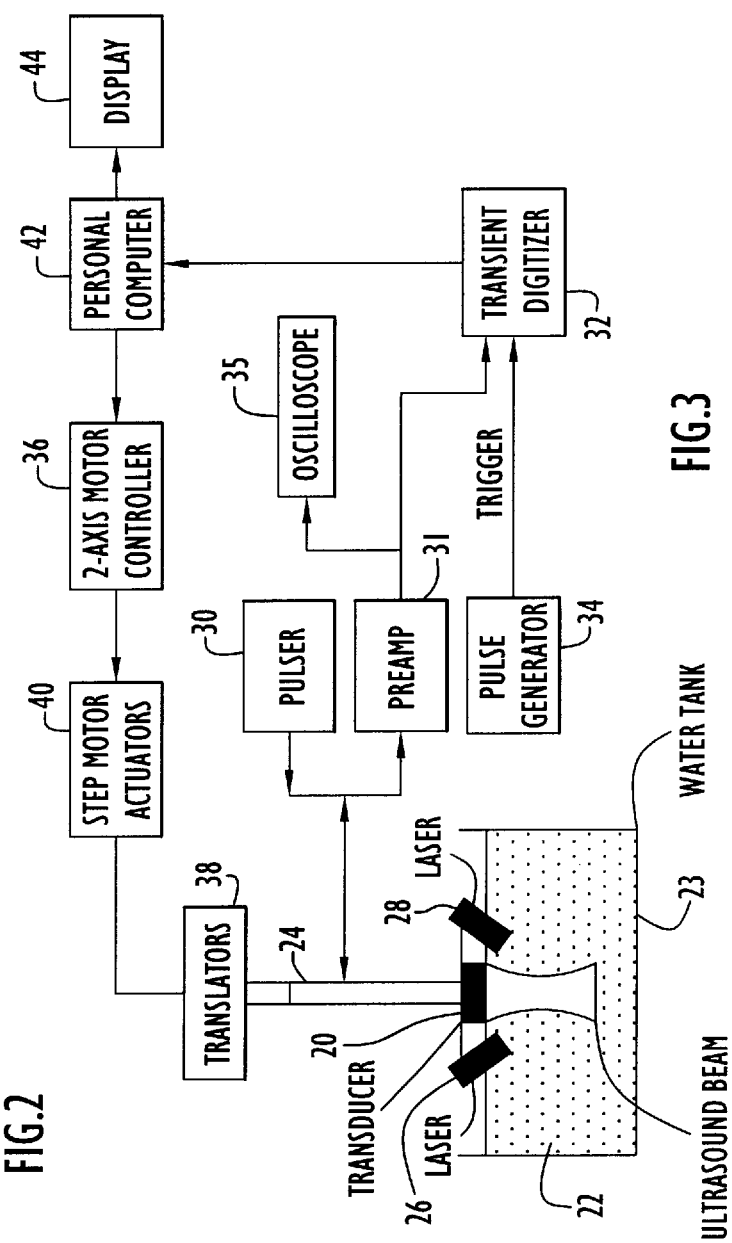
FIG. 3 is a functional block diagram of an ultrasonic imaging system according to the present invention.

FIG. 3 is a block diagram of an ultrasound B-scan imaging system constructed to perform the processing steps shown in FIG. 1 (or FIG. 1a) in accordance with the present invention. The system employs a focused transducer 20, which is mechanically scanned over a linear path lying along a plane substantially perpendicular to the axis along which transducer 20 radiates to collect cross-sectional pulse-echo image data. Transducer 20 and a specimen are immersed in a water medium 22 contained in a water tank 23 to achieve acoustic coupling therebetween. An articulated mount arm 24 holds the transducer and two laser beams 26 and 28 which are aimed to pinpoint the focus of the ultrasound beam. The transducer is excited by a 200–400 V pulse produced by the pulser 30 of a pulser-receiver (e.g., Model 5052PR, Panametrics, Inc.). The ultrasonic pulses reflected from the tissue sample are received by transducer 20 which converts the reflected pulses to electric signals. The converted voltage signals are amplified by a pre-amplifier 31 of the receiver section of the pulser-receiver and digitized by a digitizer 32. Digitizer 32 can be, for example, an 8 bit transient digitizer (Model 2001 A, DSP Technology Inc.) or a 12 bit digitizer (Gage 8012 A/D board). A pulse generator 34 (e.g., Model 5101, Data Dynamics) serves to trigger the transient digitizer 32 for the start of data acquisition. Optionally, an oscilloscope 35 can be used to view the amplified reflected pulse prior to A/D conversion by digitizer 32.

Motion of transducer arm 24 is controlled by a two-axis step motor controller 36 (e.g., Model 6006-DB AMSI Corp.). Arm 24 is connected to two linear translation platforms 38 (Model 433 Series, Newport Corporation), which are actuated by two stepping motor linear actuators 40 (Model 701AM AMSI Corp.), providing computer-controlled motion of the transducer arm in two directions (XY). The height positioning of arm 24 (Z direction) is provided by a third translation platform which is manually driven by a micrometer.

A personal computer 42 controls operation of the system, acquires the digitized reflected pulse data, and performs the processing steps shown in FIG. 1 (or FIG. 1a). In the mechanically scanned embodiment shown in FIG. 3, computer 42, actuators 40, and step motor controller 36 serve as the scan controller. LabView software, for example, can be used to control the instrumentation and data acquisition. The resulting B-scan images are displayed on display 44 or printed on a printer (not shown).

In practice, the system of the present invention can be implemented using dedicated VLSI processors, with the signal drivers and signal processing circuitry being assembled on a single circuit board. The transducer preferably comprises an array of small ultrasound transducer elements mounted in a flexible pad which can be placed on the skin of a patient and which is connected by a cord to the processing board. The array of transducer elements can be phase controlled to effect electronic scanning of a region of interest in less than one minute, thereby eliminating the need for mechanical scanning mechanisms. Specifically, the computer controls pulser and transducer to effect electronic scanning in any of the following formats: linear, steered linear, sector and circular.

To simplify operation and reduce processing, the reflection profile i(t) or spectrum I(f) of the incident pulse can be determined when the system is manufactured and stored in an on-board memory. Optionally, the profile or spectrum of the incident pulse can be re-determined by periodic calibration or calibration before each use.

Advantageously, the system can be used with standard personal computers which are available in hospitals and doctors' offices, making it simpler and less expensive to perform clinical trials. According to another embodiment, a notebook size assembly that can be hand carried contains all the modular elements of the system including a keyboard to enter patient information and image output capability which allows for remote transmission of the data collected over a network or phone lines via a fiber optic medium, wires or through free space (i.e., the atmosphere or outer space). The system preferably has a modular design capable of accommodating plug-in assemblies so that new functional capabilities can be introduced into the equipment.

Experimental results in the following experiments were obtained by calculating and displaying the acoustic impedance from the incident ultrasound signals and the ultrasound signals reflected from a specimen. The process of the present invention primarily improves resolution in the depth dimension, and the experiments described hereinbelow were designed to demonstrate improvement in the spatial depth resolution. Accordingly, these experiments did not include measures specifically designed to improve lateral resolution (which was on the order of 1 mm), and lateral resolution was determined primarily by the transducer beamwidth and the lateral spacing between adjacent pulses (due to scanning).

Experiment 1

Experiment 1 demonstrates the improvement in image quality obtained using the acoustic impedance reconstruction technique of the present invention with simple phantom (i.e., non-tissue) specimens. In Experiment 1, the ultrasound transducer 20 was laterally scanned by computer-controlled translation platform 38 (FIG. 3) to acquire cross-sectional image data. The incident ultrasound profile i(t) was determined from acquisition of the reflection profile from an aluminum block placed at the focal length of the transducer and inversion of the digitized signal in time.

Two phantoms were used which consisted of: 1) an aluminum block; and 2) a thin piece of soft plastic with a thickness of 0.7 mm. The aluminum block was placed at the bottom of water tank 23, and the radiating surface of transducer 20 was positioned at a perpendicular distance equal to the transducer's focal length above the surface of the aluminum block. Tank 23 was filled with water so that the radiating surface of transducer 20 and the tip of the laser beam assembly 26/28 were submerged.

The second phantom was constructed from a piece of soft plastic, with dimensions of 2×4 cm. The phantom was placed on top of the rubber mount designed for supporting the samples.

Ultrasound pulse-echo B-scan images of the phantoms were acquired by scanning the transducer laterally and combining adjacent rectified longitudinal scans to create an image. A 5 MHz transducer was excited with a high voltage amplitude pulse (~200V) from pulser 30 of the pulser-receiver. The backscattered signals from the transducer were amplified with a receiver gain of 20 dB and then attenuated 34 dB for the first phantom, and 18 dB for the second phantom so that the maximum dynamic range of digitizer 32 was not exceeded. The resulting signals were digitized at a sampling rate of 100 MHz.

The pulse-echo B-scan data was deconvolved to obtain the target impulse response image. In accordance with the processing steps shown in FIG. 1, the deconvolution algorithm included: 1) division of the backscattered pulse spectrum by the incident pulse spectrum for each scan; 2) multiplication of the computed spectrum of each scan by a window to suppress the contribution of frequencies outside the bandwidth of the power spectrum of the transducer; and 3) application of an inverse Fourier transform operation to the windowed spectrum of each scan to restore an impulse response image. A rectangular window was utilized. The conversion from the impulse response to the acoustic impedance was performed for each scan using equation 10.

The pulse-echo image from the aluminum block is shown in FIG. 4a. The bright reflection corresponds to the edge of the aluminum block. The other reflections correspond to Gibbs' phenomenon-like oscillations caused by the shape of the incident pulse. FIG. 5a shows the pulse-echo image of the plastic phantom. The two relatively brighter reflections correspond to the top and bottom edge of the plastic film, respectively.

The impulse response image of the aluminum block is shown in FIG. 4b. The sharp cutoff of the rectangular window in the frequency domain causes Gibbs' phenomenon oscillations to appear in the impulse response image. The impulse response image of the plastic phantom is shown in FIG. 5b.

The acoustic impedance image of the aluminum block is shown in FIG. 4c. The acoustic impedance image of the plastic phantom is shown in FIG. 5c. The grey-scale bars shown in FIGS. 4a–4c and 5a–5c are log scales of absolute voltage, impulse response magnitude, and relative acoustic impedance, respectively.

Figure 6A:
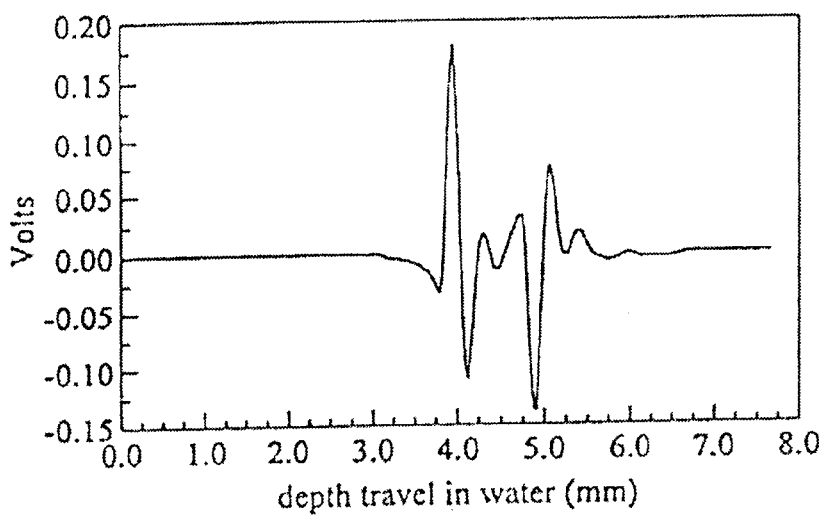
FIGS. 6a–6c respectively illustrate the pulse-echo voltage, impulse response, and acoustic impedance profiles for a single A-scan from the plastic phantom.
Figure 6B:
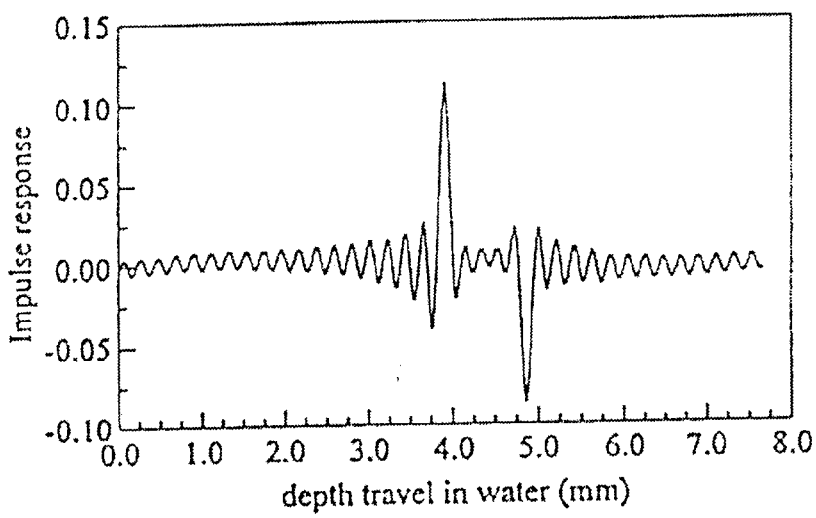
Figure 6C:
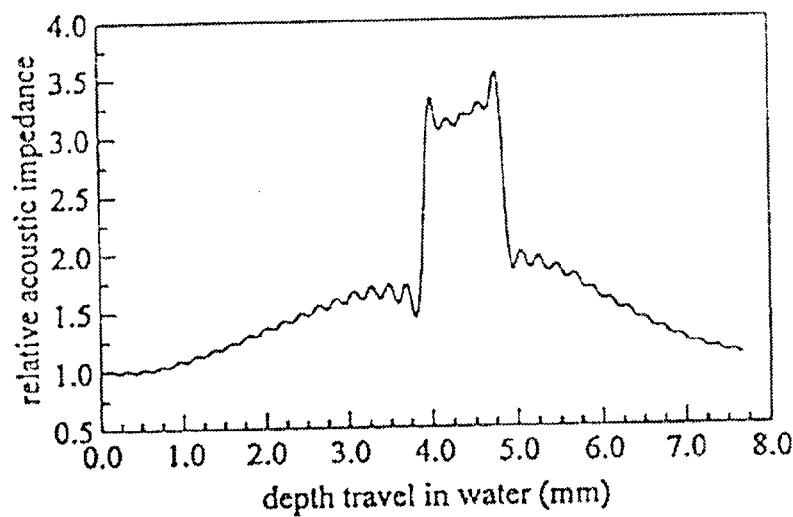
Figure 7B:
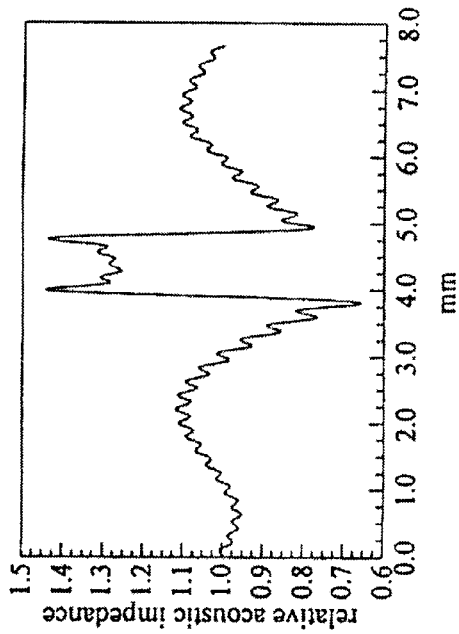
FIGS. 7a–7d are A-scan acoustic impedance profiles which illustrate the effect of low frequencies on the acoustic impedance profile reconstruction of the plastic phantom.
Figure 7D:
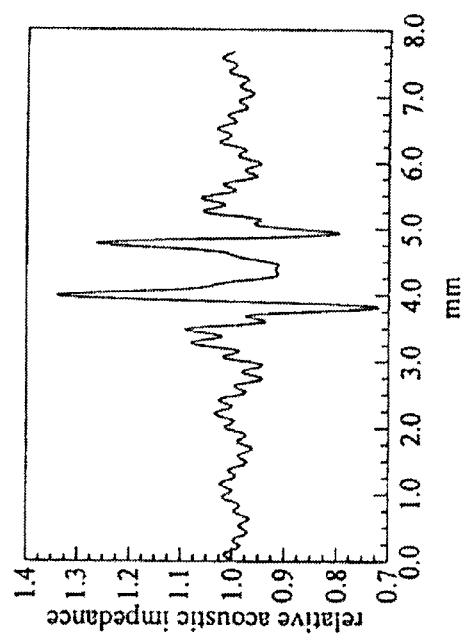
Figure 7A:
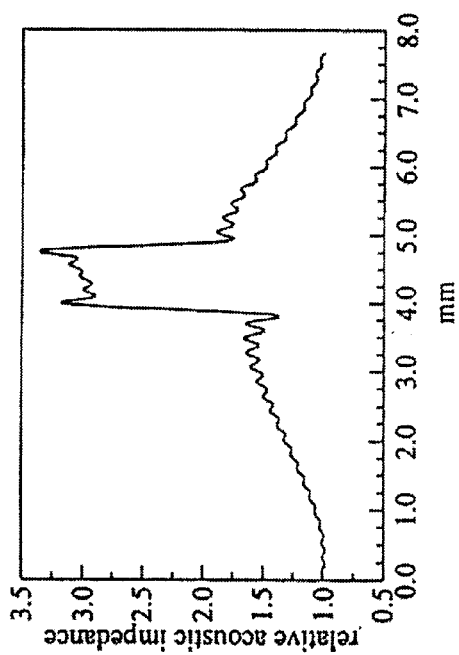
Figure 7C:
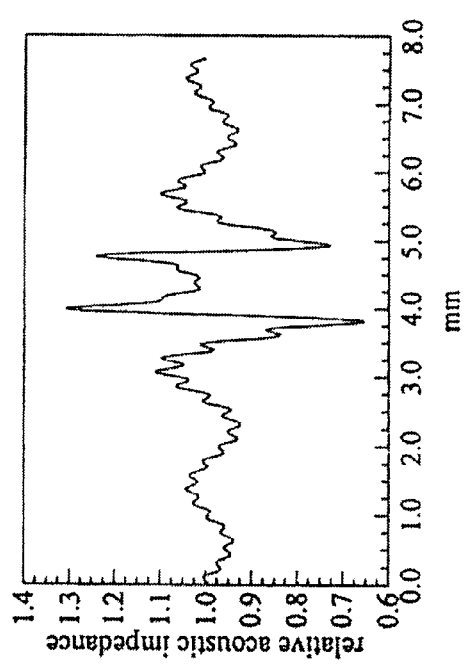
Figure 8A:
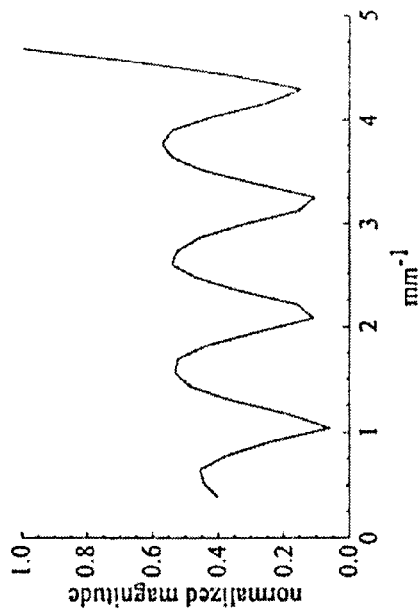
FIGS. 8a–8d illustrate the computed transfer functions corresponding to the acoustic impedance profiles shown in FIGS. 7a–7d.
Figure 8B:
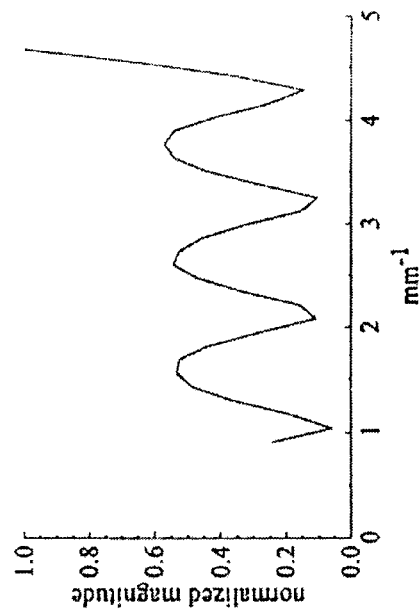
Figure 8C:
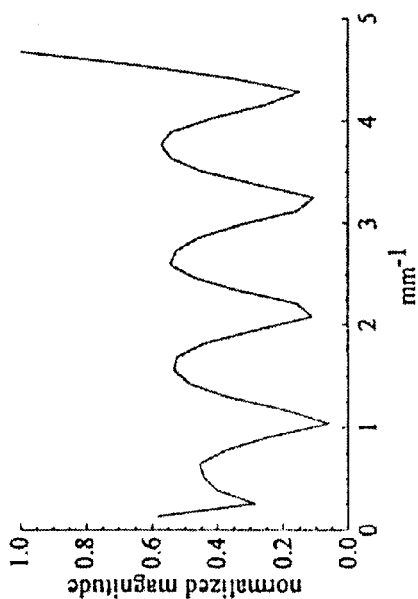
Figure 8D:
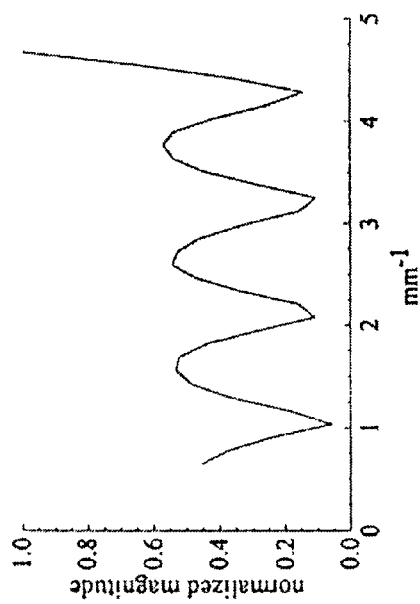
Figure 9A:
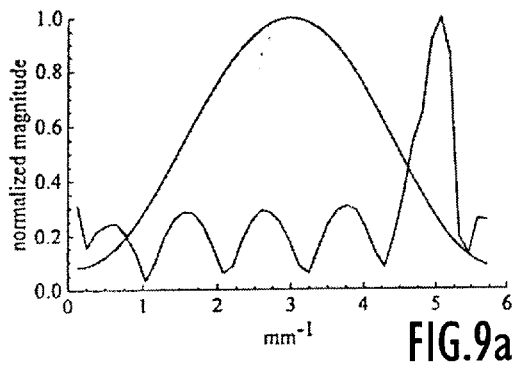
FIGS. 9a–9f illustrate the computed transfer function magnitudes and the corresponding reconstructed acoustic impedance profiles with Hamming, Hanning, and Blackman windows.
Figure 9B:
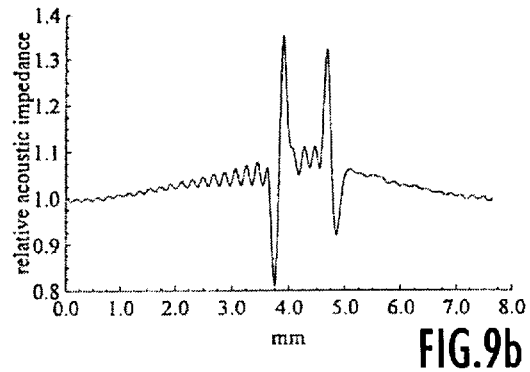
Figure 9C:
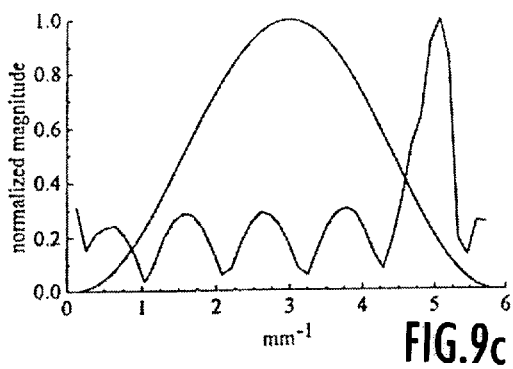
Figure 9D:
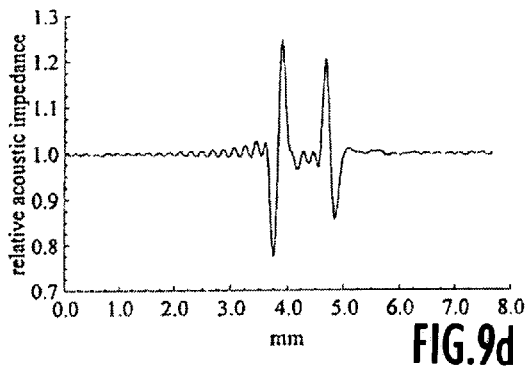
Figure 9E:
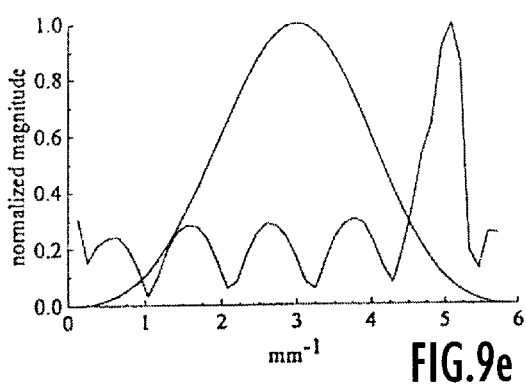
Figure 9F:
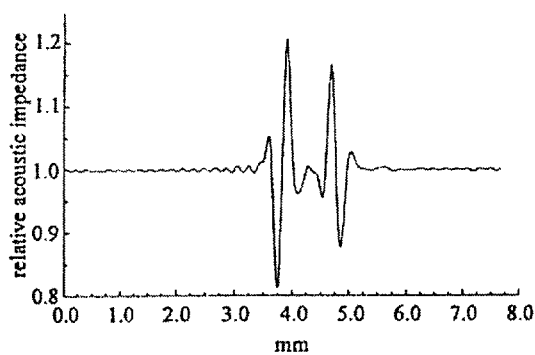

FIGS. 6a–6c show A-scan profiles of the pulse-echo response, impulse response, and relative acoustic impedance for the plastic phantom, respectively.

For the aluminum block, the recovery of the acoustic impedance resulted in an improvement in both image quality and image resolution as compared with the original pulse-echo image. The edge of the aluminum block is much more clearly resolved in the acoustic impedance image as compared with the original pulse-echo image. As previously explained, the sharp cutoff rectangular window function preserves the low frequency components of the computed spectrum for inclusion in the estimation of the impulse response.

For comparison, Hanning, Hamming, and Blackman windows were also applied to the transfer function; however, although impulse response images with less ringing could be restored, the suppression of the valuable low frequency information in the computed spectrum due to the gradual cutoff of the windows caused a degradation in the reconstruction of the acoustic impedance image.

FIGS. 7a–7d show A-scan acoustic impedance profile reconstructions of the plastic phantom after setting the magnitudes of a number of low frequency components in the computed transfer function equal to zero. Specifically, the acoustic impedance profiles shown in FIGS. 7a–7d resulted from setting the low frequency cutoffs at 0.13 mm$^{-1}$, 0.39 mm$^{-1}$, 0.65 mm$^{-1}$ and 0.91 mm$^{-1}$, respectively (the higher spatial frequency cutoff was 4.68 mm$^{-1}$ for all cases). The corresponding computed transfer functions are shown in FIGS. 8a–8d. These profiles demonstrate that low frequencies down to the DC level play an important role in calculation of the acoustic impedance profile: if the low frequency part of the spectrum of the pulse-echo data is absent, the recovered acoustic impedance profile loses its large-scale trend. Thus, the absence of low frequency information in the data makes the recovery of the acoustic impedance highly unstable, and small uncertainties in the low frequency part of the data lead to large oscillations in the recovered acoustic impedance. Of course, as explained above, where the transducer has poor low frequency characteristics, elimination of a small number of low frequency components of the transfer function improves the acoustic impedance image without unduly degrading the large-scale structure of the acoustic impedance (see Experiment 4).

The reconstruction of the acoustic impedance profile of the plastic phantom with a Hamming, Hanning, and Blackman window applied at a lower spatial frequency of 0.13 mm$^{-1}$ and terminated at a spatial frequency of 5.72 mm$^{-1}$ in the computed transfer function are illustrated in FIGS. 9a–9f. The impedance reconstructions do not contain the large scale aspects of the plastic phantom's acoustic impedance profile.

Processing of acquired pulse-echo B-scan images of the phantoms demonstrates that deconvolution of the pulse-echo image results in improvement of resolution, and the reconstruction of the acoustic impedance results in an improvement in image quality of the processed images as compared with the pulse-echo image. The low frequencies down to the DC level in the reflected spectrum play an important role in the reconstruction of the large scale aspects of the acoustic impedance.

Experiment 2

Experiment 2 demonstrates the improvement in the image quality of tissue specimens as a function of transducer frequency using the acoustic impedance reconstruction technique of the present invention. In Experiment 2, fifteen surgically resected human colon tissue specimens were used for acquisition of in vitro pulse-echo image data. Tissue samples approximately 2×4 cm in size were dissected from the specimens, marked for an imaging site, and attached to the rubber mount with pins. The mount was then submerged in water tank 23 and transducer mount arm 24 was aligned for acquiring images from the marked sites. The focal spot of transducer 20 was placed approximately in the center of the tissue thickness, so that an optimal depth of focus could be achieved in imaging through the specimen thickness.

In vitro ultrasound pulse-echo data was obtained by scanning transducer 20 laterally and acquiring axial scans of backscatter versus depth. Transducer 20 was excited with a high-voltage amplitude pulse from the pulser section of the pulser receiver. The backscatter signal was amplified 100 times (40 dB), attenuated at a suitable setting, and digitized with a sampling frequency of 100 MHz. In five cases, ten times averaged backscattered signals (A-scans) were acquired to reduce noise and improve image quality prior to post-processing.

The pulse-echo B-scan data was deconvolved to obtain the tissue impulse response image. In accordance with the processing steps shown in FIG. 1, the deconvolution algorithm included: 1) division of the backscattered spectrum by the incident pulse spectrum for each scan; 2) multiplication of the computed spectrum of each scan by a window to suppress the contribution of frequencies outside the bandwidth of the incident power spectrum of the transducer; and 3) application of an inverse Fourier transform operation to the windowed spectrum of each scan to restore an impulse response image. The conversion from the impulse response to the acoustic impedance was performed for each scan using equation 10.

Figures 10A, 10B, 10C:
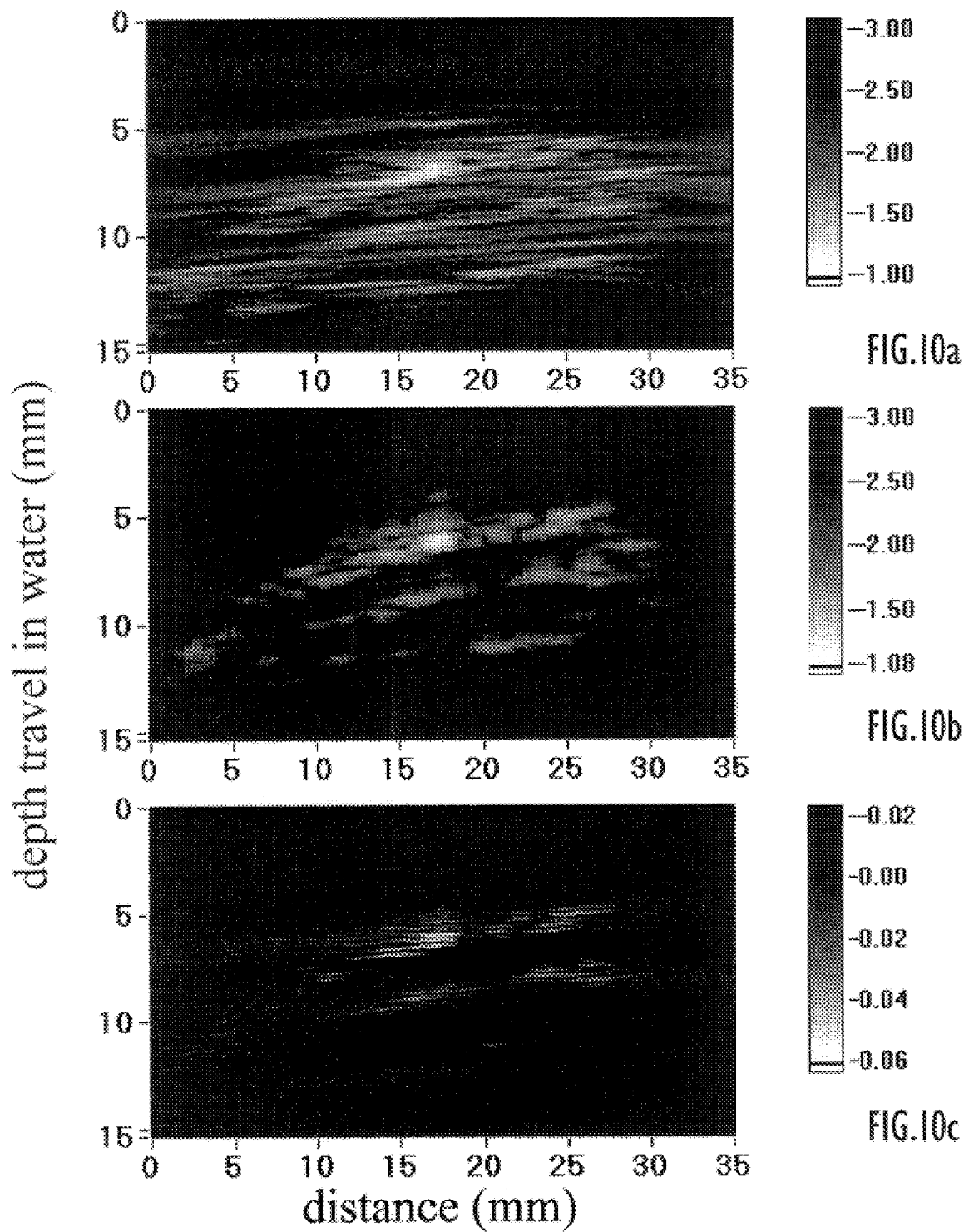
FIGS. 10a–10c respectively illustrate the pulse-echo, impulse response, and acoustic impedance B-scan images from an in vitro colon specimen obtained with a 5 MHz transducer.
Figures 12A, 12B, 12C:
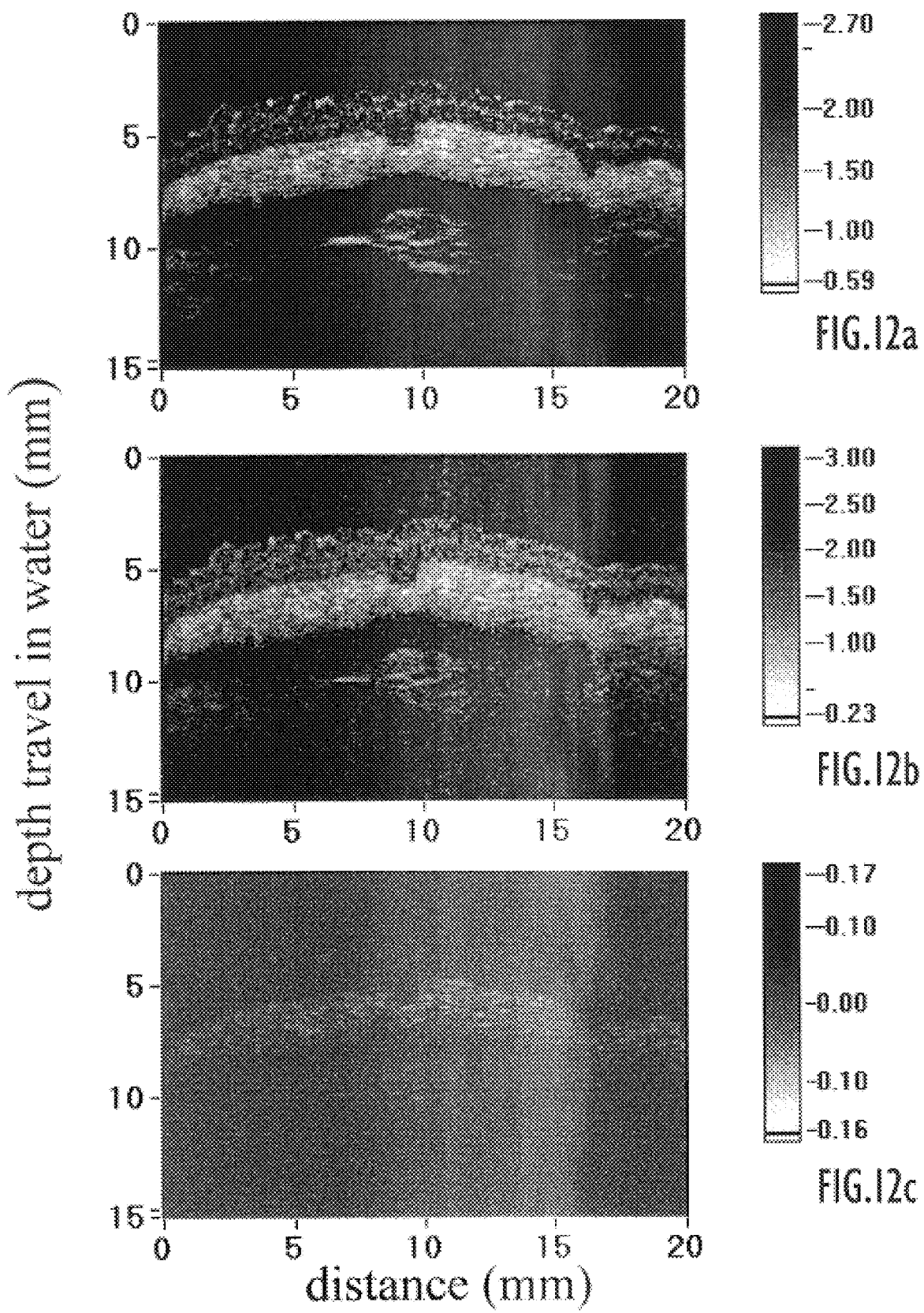
FIGS. 12a–12c respectively illustrate the pulse-echo, impulse response, and acoustic impedance B-scan images from an in vitro colon specimen obtained with a 25 MHz transducer.

The pulse-echo B-scan image, the impulse response B-scan image, and the reconstructed acoustic impedance B-scan image of an in vitro colon specimen with a 5 MHz transducer are respectively shown in FIGS. 10a–10c.

Figure 13:
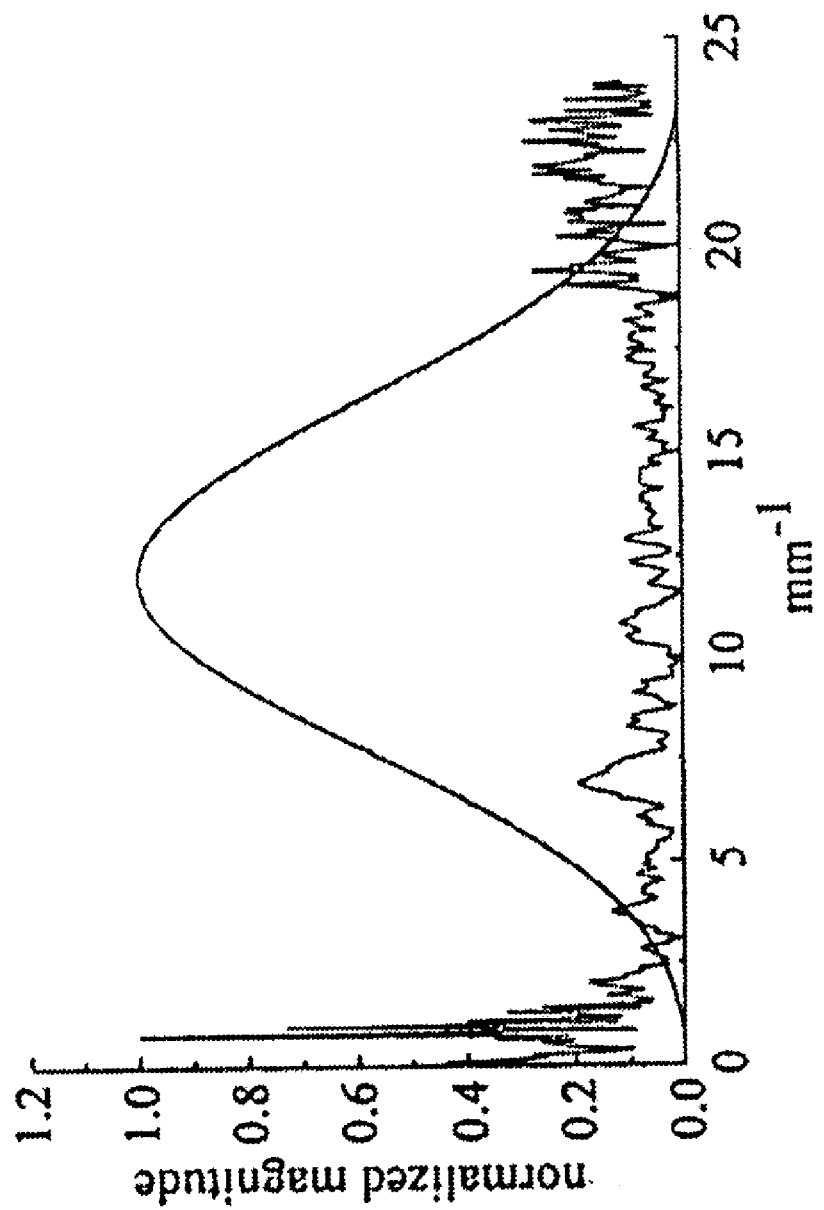
FIG. 13 is a graph illustrating a computed tissue transfer function and the Blackman window used for estimation of the impulse response and reconstruction of relative acoustic impedance profile shown in FIGS. 12b and 12c.
Figure 14A:
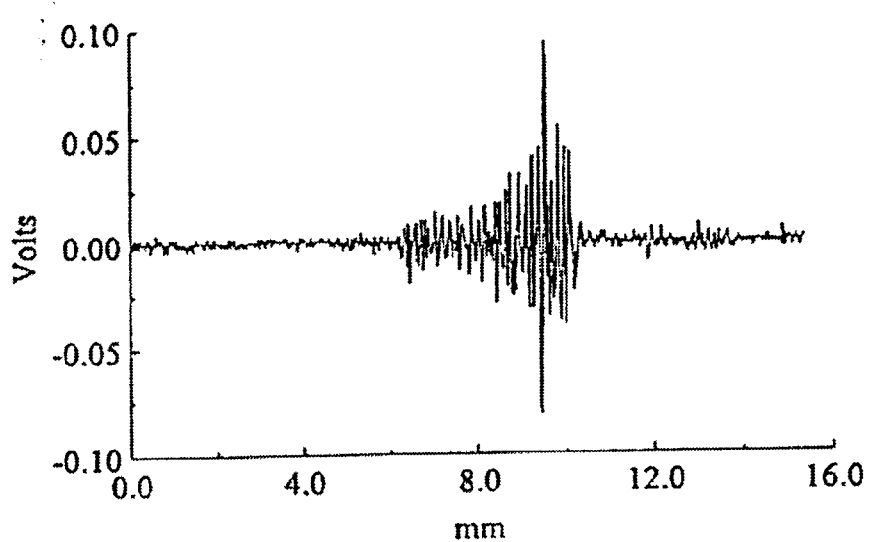
FIGS. 14a–14c respectively illustrate the pulse-echo, impulse response, and relative acoustic impedance A-scan profiles of a tissue specimen obtained with a 20 MHz transducer.
Figure 14B:
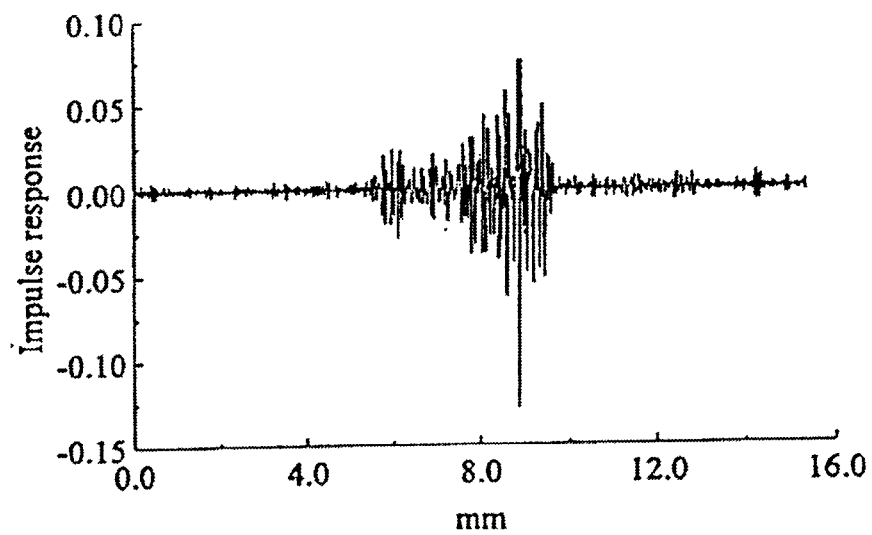
Figure 14C:
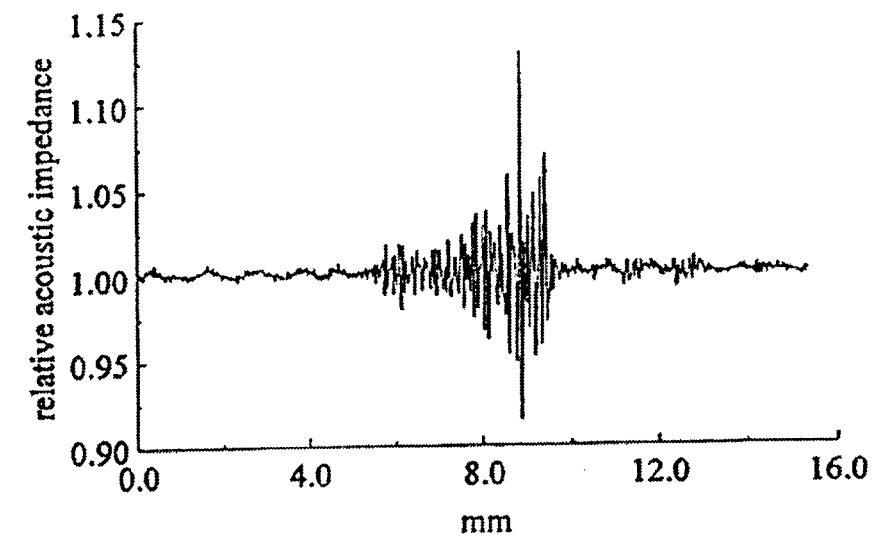

The in vitro pulse-echo, impulse response, and reconstructed acoustic impedance B-scan images obtained with a 20 MHz transducer and a 25 MHz transducer from a colon specimen are shown in FIGS. 11a–11c and 12a–12c, respectively. Although higher resolution pulse-echo images are obtained with the 20 and 25 MHz transducers, the recovered acoustic impedance images are degraded as compared to the original pulse-echo images. From the measured power spectrum for the three transducers (not shown), it can be observed that the spectrum for the low frequencies is much more degraded with the 20 and 25 MHz transducers than with the 5 MHz transducer, which in turn degrades the acoustic impedance image. FIG. 13 shows the computed transfer function of a single A-scan profile obtained with the 20 MHz transducer from a tissue specimen, together with the Blackman window used for estimation of the impulse response image and reconstruction of the relative acoustic impedance image respectively shown in FIGS. 11b and 11c. The lower spatial frequencies below approximately 1 $mm^{-1}$ are degraded, giving rise to high magnitude values in the computed transfer function. FIGS. 14a–14c respectively show the pulse echo profile, the estimated impulse response profile, and the reconstructed acoustic impedance profile for a single A-scan obtained with the 20 MHz transducer. It can be deduced that the recovery of the acoustic impedance in tissues is limited due to the degradation of the low frequency information in the data obtained from the tissues. The Blackman window shown in FIG. 13 was applied at a lower spatial frequency of 0.0651 $mm^{-1}$ and terminated at a spatial frequency of approximately 24 $mm^{-1}$.

Experiment 3

Figure 15A:
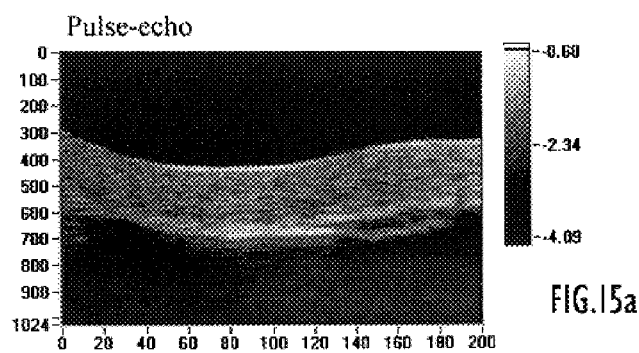
FIGS. 15a–15c respectively illustrate the pulse-echo, impulse response, and relative acoustic impedance B-scan images of a pig artery generated with a 20 MHz transducer.
Figure 15B:
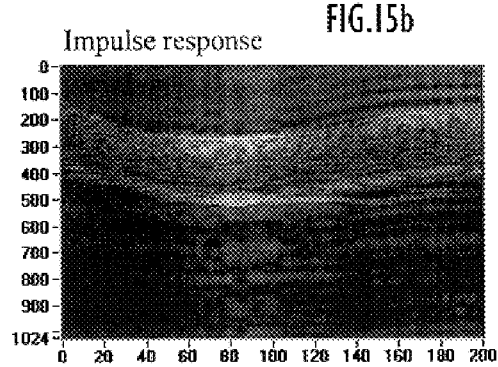
Figure 15C:
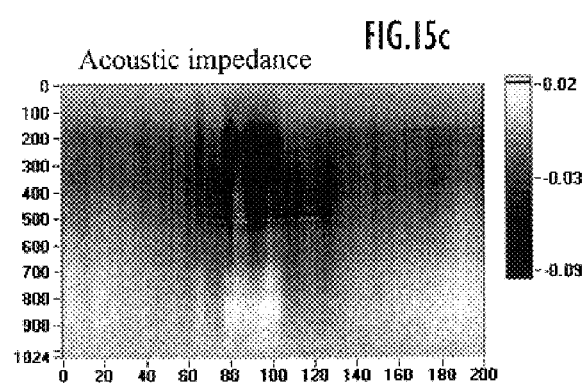

Experiment 3 demonstrates the improvement of the acoustic impedance B-scan image with a lower transducer frequency. In Experiment 3, B-scan images of a pig artery were generated with a 20 MHz transducer and a 3.5 MHz transducer. With the 20 MHz transducer, the pulse-echo image shown in FIG. 15a was acquired using an 8-bit digitizer with 100 MHz sampling at a receiver attenuation setting of 32 dB. The impulse response and acoustic impedance images shown in FIGS. 15b and 15c, respectively, were obtained using a rectangular window and eliminating the lowest frequency point in the transfer function. Comparing FIGS. 15a and 15c, it can be seen that the acoustic impedance image is severely degraded. Again, this is due primarily to the transducer's poor low-frequency characteristics.

The pulse-echo images of the four pig artery samples shown in FIGS. 16a, 16b, 17a and 17b were acquired using a 3.5 MHz transducer and an 8-bit digitizer with 50 MHz sampling and 100 times averaging. The reconstructed acoustic impedance images shown in FIGS. 16c, 16d, 17c and 17d were compared with obtained histology section from the imaged cross-sections to determine whether observed layers in the impedance images correspond to the actual histological layers.

The histology sections corresponding to the imaged cross-sections constituted of a very thin intima layer, a media layer and the adventitia layer. The intima layer is most likely not resolved in these images considering the theoretical limit of the transducer.

As can be seen by comparing FIGS. 16a, 16b, 17a, and 17b with FIGS. 16c, 16d, 17c, and 17d, at a transducer frequency of 3.5 MHz, the acoustic impedance images are superior to the corresponding pulse-echo images. In particular, the tissue layers are more clearly resolved in the acoustic impedance images, and the speckle present in the pulse-echo images is not present in the acoustic impedance images. Further, by comparing FIG. 15a with FIGS. 16c, 16d, 17c, and 17d, it can also be seen that the 3.5 MHz acoustic impedance images are superior to the 20 MHz pulse-echo image in terms of resolution and speckle.

Experiment 4

Experiment 4 demonstrates the effect of varying the field of view (FOV) on the acoustic impedance B-scan image. Experiment 4 also demonstrates the effect of changing the position of the low frequency cutoff of the frequency domain window function applied to the transfer function. In Experiment 4, 3.5 MHz pulse-echo images of a three layer plastic phantom were acquired with an 8 bit digitizer at a 50 MHz sampling rate. B-scan images were formed with three different field of views (FOV) corresponding to 512, 1024 and 2048 depth sample points (with greater depth sampling points corresponding to a greater field of view). The pulse-echo signals were processed to obtain the impulse response and the acoustic impedance. For each FOV, a rectangular window was applied with the low frequency cutoff at three different frequency points.

Figure 18A:
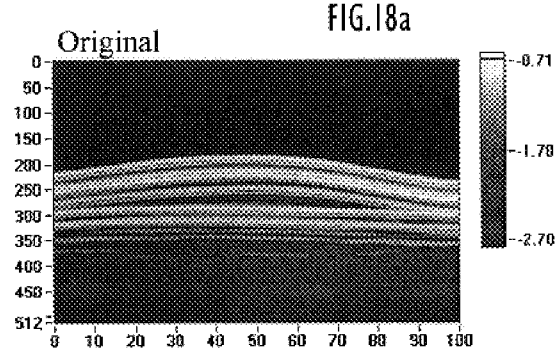
FIGS. 18a–18d respectively illustrate, for a field of view corresponding to 512 depth sample points, the pulse-echo B-scan image of a plastic phantom and the corresponding acoustic impedance B-scan images with three different rectangular window functions.
Figure 18B:
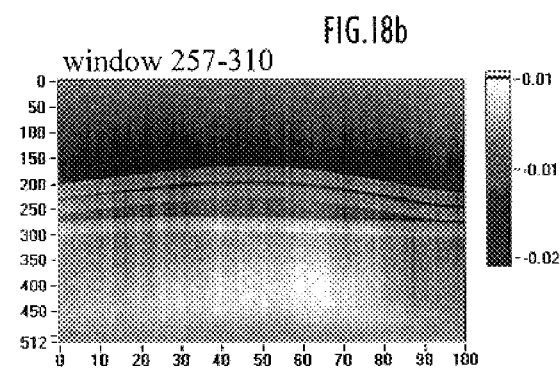
Figure 18C:
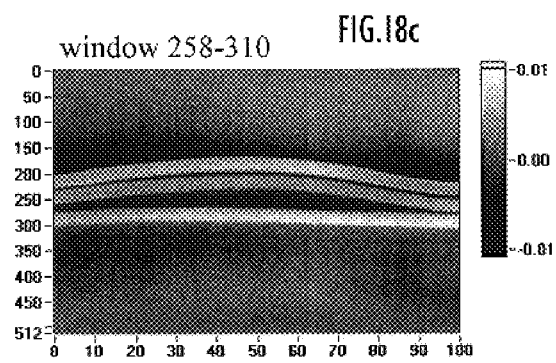
Figure 18D:
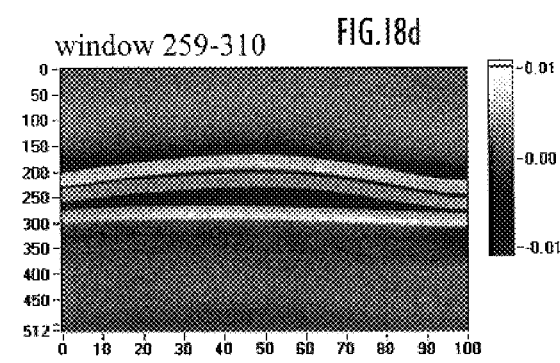

FIG. 18a shows the pulse-echo response for the 512 point FOV. The acoustic impedance calculated with a rectangular window covering the transfer function frequency components 257–310 (256 corresponds to DC) is shown in FIG. 18b. FIGS. 18c and 18d show the acoustic impedance image where the low frequency cutoff is moved to frequency components 258 and 259, respectively (the upper cutoff remained the same). As can be seen from FIGS. 18a–18d, each of the acoustic impedance images is superior to the pulse-echo image. Further, the acoustic impedance image improves as the low frequency cutoff is moved from the first component after the DC term (257) to the second component (258), and improves further when moved to the third component (259) after the DC term. This improvement results from elimination of the corruption in the lowest frequency components of the transfer function due to the limited bandwidth of the transducer. Importantly, removal of these low frequency components does not impact the large scale features of the acoustic impedance to the extent that the resulting B-scan image is degraded, and the intermediate scale features of interest in the acoustic impedance image, which are represented by the intermediate frequencies of the transfer function, are not affected.

FIGS. 19a–19d show the pulse-echo B-scan image and acoustic impedance images for three different low frequency cutoffs for the 1024 depth sample point FOV case, and FIGS. 20a–20d show the corresponding images for the 2048 depth sample point FOV case. As with the 512 point FOV case, the acoustic impedance image is superior to the pulse-echo image for the 1024 and 2048 point FOV cases. Further, as with the 512 point FOV case, the acoustic impedance improves as the low frequency cutoff is moved from the first frequency component after the DC term to the second and third components. Specifically, as shown in FIGS. 19b–19d, the image quality improves as the window is changed from frequency components 513–619 (512 corresponds to DC) to 514–619 and then to 515–619. Similarly, as shown in FIGS. 20b–2d, the image quality improves as the window is changed from frequency components 1025–1262 (1024 corresponds to DC) to 1026–1262 and then to 1027–1262.

Comparing FIGS. 18d, 19d and 20d, it can further be seen that the quality of the acoustic impedance image is best with the smallest FOV. Specifically, the acoustic impedance B-scan image acquired with the 512 point FOV is superior to that acquired with the 1024 point FOV and to that acquired with the 2048 point FOV, particularly in terms of contrast.

Experiment 5

Figure 21A:
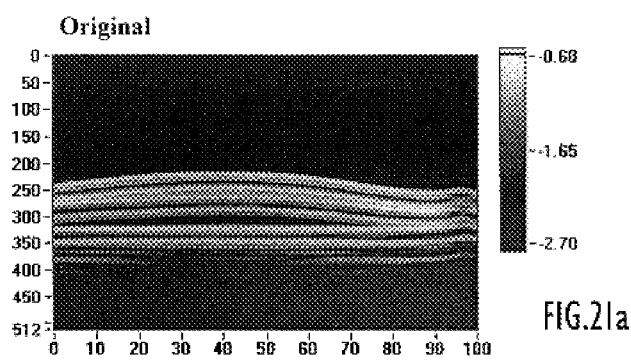
FIGS. 21a–21c respectively illustrate a pulse-echo B-scan image of a three-layer plastic phantom using a 3.5 MHz transducer, the acoustic impedance B-scan image of the plastic phantom obtained without performing prefiltering of the pulse-echo signal, and the acoustic impedance B-scan image of the plastic phantom obtained with prefiltering.
Figure 21B:
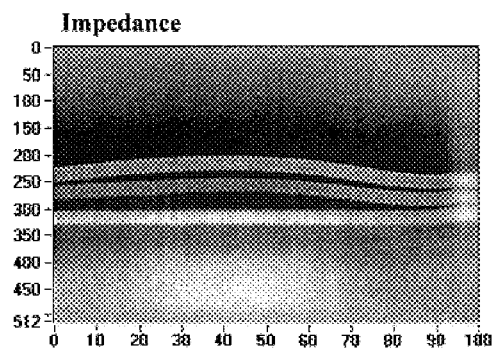
Figure 21C:
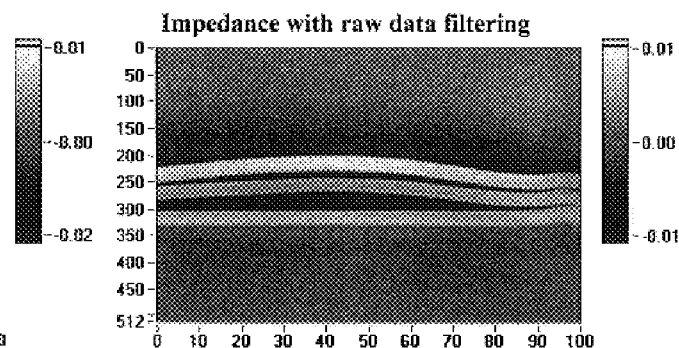

In Experiment 5, the effect of performing RF prefiltering on the incident and reflected pulse-echo signals is demonstrated. FIG. 21a shows the pulse-echo B-scan image of a three-layer plastic phantom using a 3.5 MHz transducer. FIG. 21b shows the acoustic impedance B-scan image of the plastic phantom obtained without performing prefiltering of the pulse-echo signal. FIG. 21c shows the acoustic impedance B-scan image of the plastic phantom obtained with prefiltering. Specifically, a time-domain Hamming window was applied to each A-scan in the raw data, to force end points of the A-scans to have equal amplitude values, in order to reduce the effects of leakage caused by the FFT calculation. The windowed data was then processed to obtain the impulse response estimation and acoustic impedance reconstruction. It can be seen by comparing FIGS. 21b and 21c that prefiltering improves the image quality of the acoustic impedance image, particularly in terms of contrast.

FIGS. 22a–22c respectively show the pulse-echo B-scan image, the acoustic impedance B-scan image without prefiltering, and the acoustic impedance B-scan image with prefiltering for a pig artery specimen sampled with a 12 bit digiter. FIGS. 23a–23c show corresponding images for a pig artery specimen sampled with an 8-bit digitizer. Here again, the prefiltering improves the image quality of the acoustic impedance B-scan images.

Experiment 6

Experiment 6 demonstrates the improvement in the image contrast of the acoustic impedance B-scan image with decreasing transducer frequency. Further, Experiment 6 demonstrates that the resolution of a 3.5 MHz transducer acoustic impedance B-scan image is superior to that of a 20 MHz pulse-echo B-scan image.

Pulse-echo B-scan images from a three-layer plastic phantom were acquired with an 8 bit digitizer using three different transducers having center frequencies of 3.5, 5 and 20 MHz. The sampling rate was 50 MHz for the images obtained by the 3.5 and 5 MHz transducers, and 100 MHz for the image obtained by the 20 MHz transducer.

Figures 24E, 24F:
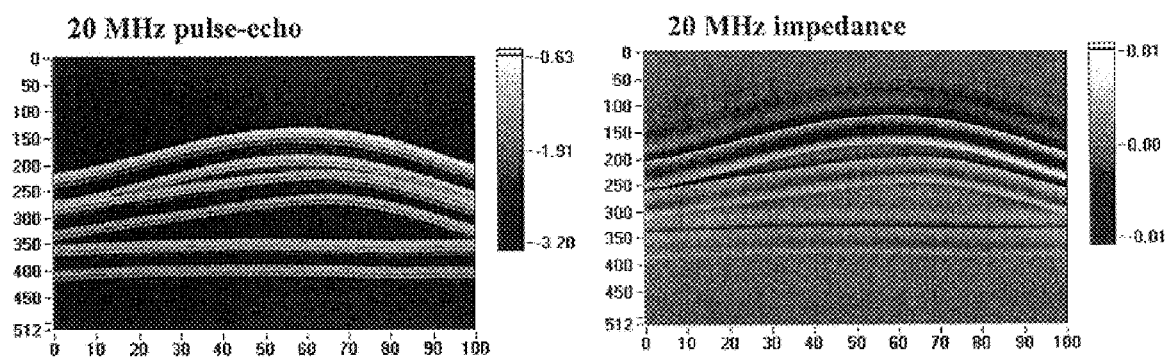

FIGS. 24a, 24b and 24c respectively show the pulse-echo B-scan images of the phantom using the 3.5, 5 and 20 MHz transducers. Note that the resolution of the pulse-echo images increases with increasing transducer frequency, as one would expect. FIGS. 24d, 24e and 24f respectively show the acoustic impedance B-scan images of the phantom using the 3.5, 5 and 20 MHz transducers. FIGS. 24d–f demonstrate that the image contrast of the acoustic impedance image increases with decreasing transducer frequency, provided that the transducer has sufficient bandwidth to capture the intermediate frequency characteristics of the specimen.

FIGS. 25a and 25b provide a side-by-side comparison of the pulse-echo B-scan image from the 3.5 MHz transducer and the superior pulse-echo B-scan image from the 20 MHz transducer. FIGS. 26a and 26b provide a side-by-side comparison of the pulse-echo image from the 20 MHz transducer and the superior acoustic impedance B-scan image from the 3.5 MHz transducer. (The superior resolution of the acoustic impedance image from the 3.5 MHz transducer relative to that of the pulse-echo image from the 20 MHz transducer can also been seen by comparing FIG. 24c with FIG. 24e.) Thus, at a 3.5 MHz transducer frequency, the present invention offers superior spatial depth resolution than conventionally available with a 20 MHz transducer frequency, while benefitting from the inherently superior depth penetration at this lower frequency.

Experiment 7

Figure 27A:
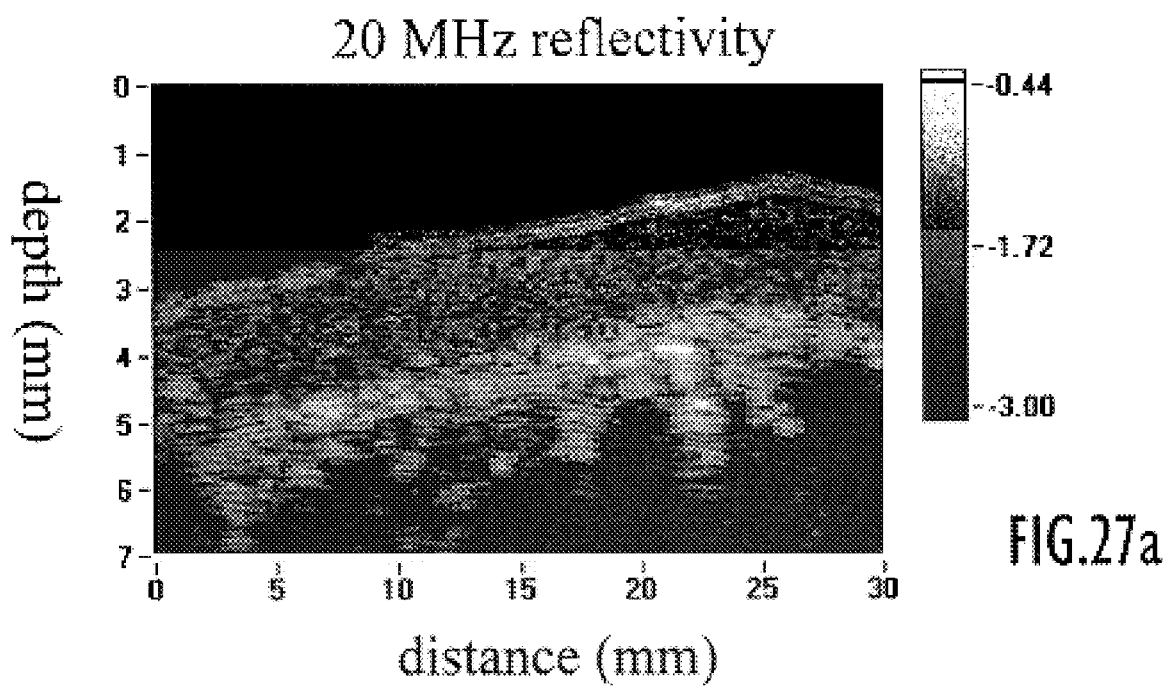
FIGS. 27a and 27b respectively illustrate a pulse-echo image of a human aorta wall using a 20 MHz transducer and an acoustic impedance image of the human aorta wall using a 3.5 MHz transducer.
Figure 27B:
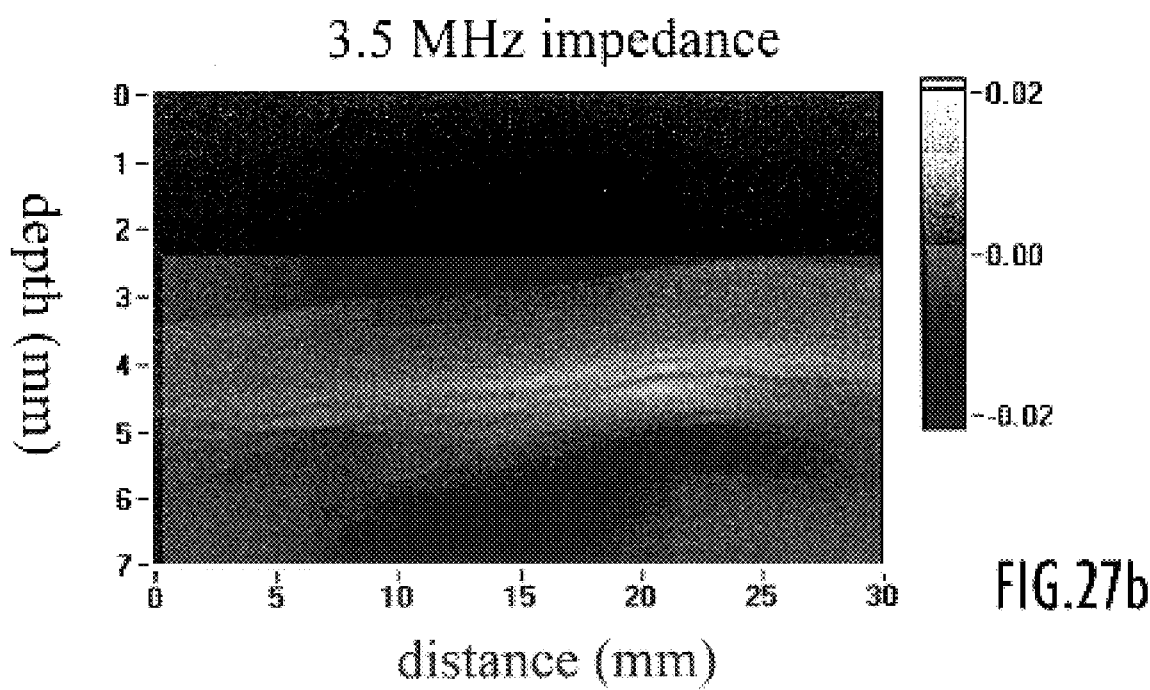

Experiment 7 demonstrates the reduction of speckle achieved with the acoustic impedance imaging process of the present invention. FIG. 27a shows a pulse-echo B-scan image of a human aorta wall using a 20 MHz transducer. FIG. 27b shows the acoustic impedance B-scan image of the human aorta wall using a 3.5 MHz transducer. The speckle (the bright spots) seen throughout the pulse-echo image is not present in the acoustic impedance image.

Figure 28A:
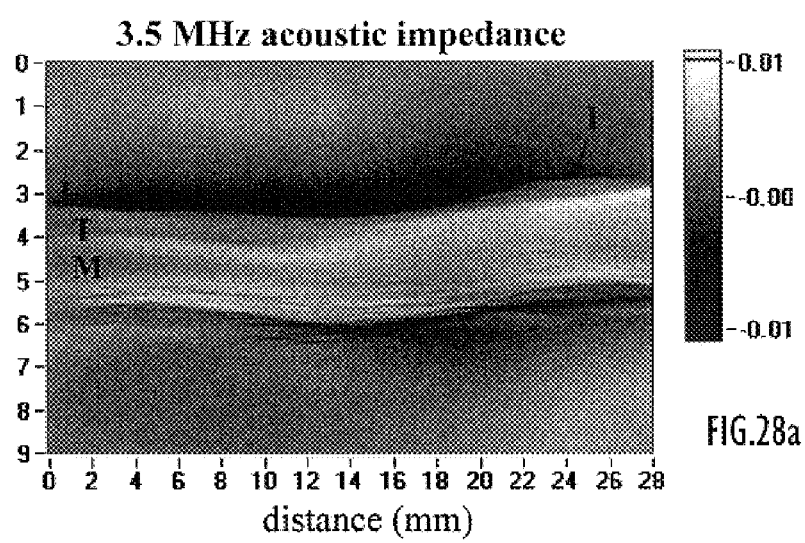
FIGS. 28a and 28b respectively illustrate an acoustic impedance B-scan image of a human aorta wall using a 3.5 MHz transducer and a histology microscope image of the human aorta specimen.
Figure 28B:
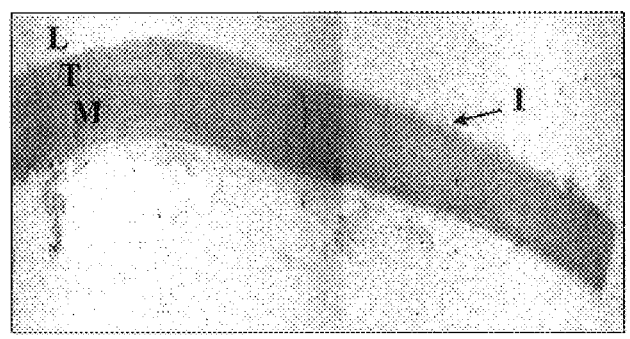

FIGS. 28a and 28b respectively illustrate an acoustic impedance B-scan image of a human aorta wall using a 3.5 MHz transducer and a histology microscope image of the human aorta specimen. Note that the lumen and the intimal and medial layers are clearly resolved in the acoustic impedance image. Further, thickening of the intimal layer (denoted by T in the figures) can be clearly seen in the acoustic impedance image, in correlation with the thickening seen in the histology section.

The system of the present invention is capable of producing images useful for diagnosing and monitoring of: cancerous growths; soft tissue and internal organ damage; bone fractures and microfractures; radiolucent and metallic foreign matter; pathological state prediction of abnormalities; healing rate; identification of non-unions; and osteoporosis. The information obtained by the system of the present invention can be used to generate two or three dimensional images that can be stored, manipulated and exchanged over a network or phone line for use in emergencies where operation preparation might be needed or in assisting in virtual consultation for analysis and diagnosis. Because of the nature of ultrasound, which has a benign effect on living tissue, the system can be used with greater frequency than other diagnostic devices and provide detailed evaluation of specific problems. This aids in developing prognoses and treatment modalities. It is also useful as an adjunct to current radiological and surgical procedures in locating and evaluating specific problem areas.

The acoustic impedance imaging system of the present invention provides several advantages over existing ultrasound imaging systems. Since conventional pulse-echo methods provide only an image of the reflectivity, standard ultrasound imaging is based on processing only this reflected ultrasound signal. The resolution that can be achieved by this approach is typically on the order of two to three wavelengths of the transmitted pulse. By using the inverse scattering theory deconvolution technique described above and relating the observed incident and reflected signal, a resolution of about one fourth of a wavelength can be achieved in high contrast situations. Thus, the resolution is enhanced by factor of 5 to 8 over that of currently used ultrasound equipment. For a 5 MHz ultrasound transducer frequency, the wavelength is 0.3 mm; therefore, it is possible to resolve fragments smaller than 0.1 mm.

The imaging system of the present invention also has several advantages over other types of conventional imaging systems. CT and MRI systems are very large machines, cost over a million dollars, cost a great deal to operate, expose a patient to radiation, do not allow for real-time diagnosis, require special facilities and highly trained personnel, do not allow for treatment while the study is being performed because of radiation danger to the physician and personnel and because instruments for treatment interfere with the diagnostic equipment, and they cannot be brought to the patient.

In contrast, the ultrasound system of the present invention comprises a small, mobile device which costs a small fraction of CT and MRI devices, costs much less per procedure (due in part to the speed of image acquisition), does not expose the patient to hazardous radiation, allows for real time diagnosis, does not require special facilities, does allow for treatment while the study is being performed since there is no radiation danger to the physician (and instruments will not interfere with the diagnostic device), and can be brought to the patient either in the hospital, home, office or battlefield. Further, the present invention produces real time images at higher resolutions than other technologies, such as X-ray. Unlike radiographic diagnostic procedures that are not in real time and that require careful monitoring and control of the levels of radiation exposure, the system causes no damaging side effects and can be used frequently without risk to the patient's safety.

Having described preferred embodiments of a new and improved method and apparatus for ultrasound imaging using acoustic impedance reconstruction, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An ultrasound imaging system, comprising:
   a transducer adapted to emit an incident ultrasonic signal toward a specimen, said transducer receiving a reflection of the incident ultrasonic signal from the specimen and generating an electrical signal which represents a reflected ultrasonic signal;
   a signal processor which reconstructs an acoustic impedance of a portion of the specimen through which the reflected ultrasonic signal passes by: computing a Fourier transform of the electrical signal which represents the reflected ultrasonic signal to obtain a reflected signal spectrum; dividing the reflected signal spectrum by a spectrum of the incident ultrasonic signal to obtain a transfer function; applying a frequency-domain window function having a sharp, low-frequency cutoff to the transfer function; computing an inverse Fourier transform of the windowed transfer function to obtain an impulse response; and calculating the acoustic impedance from the impulse response; and
   an imaging device adapted to form an image of the specimen in accordance with the reconstructed acoustic impedance.

2. The system according to claim 1, wherein said signal processor calculates the acoustic impedance by integrating and exponentiating the impulse response in accordance with a plane wave Born approximation.

3. The system according to claim 1, wherein said window function reduces to zero a magnitude of a DC component of the transfer function.

4. The system according to claim 3, wherein the magnitude of at least one of a lowest frequency component above the DC component of the transfer function, a second lowest frequency component of the transfer function and a third lowest frequency component of the transfer function is unattenuated by the window function.

5. The system according to claim 4, wherein a magnitude of the lowest frequency component of the transfer function is unattenuated by the window function.

6. The system according to claim 1, wherein the window function is a rectangular filter having a sharp, high-frequency cutoff corresponding to a high-frequency end of a bandwidth of said transducer.

7. The system according to claim 1, wherein the window function smoothly approaches zero at a high-frequency end, such that magnitudes of high-frequency components of the transfer function are gradually attenuated to zero with increasing frequency.

8. The system according to claim 1, wherein said signal processor applies a time domain pre-window to the electrical signal prior to computing the Fourier transform of the electrical signal.

9. The system according to claim 8, wherein the time domain pre-window is a Hamming window.

10. The system according to claim 1, further comprising a scan controller configured to control said transducer to emit a sequence of incident ultrasonic signals which respectively travel along adjacent lines within the specimen, said signal processor reconstructing an acoustic impedance corresponding to each of the incident ultrasonic signals.

11. The system according to claim 10, wherein said transducer is a phased-array of transducer elements, wherein a direction of each of the incident ultrasonic signals is controlled by a relative phase of individual ultrasonic signals emitted by the transducer elements.

12. The system according to claim 11, wherein said transducer is controllable by said scan controller to scan in at least one of the following scanning formats: linear; steered linear, sector, and circular.

13. The system according to claim 10, further comprising a movable platform on which said transducer is mounted, said scan controller effecting scanning by displacing said movable platform.

14. The system according to claim 10, wherein said scan controller controls said transducer to scan in a plane of the specimen, said imaging device forming a two-dimensional B-scan image of the specimen.

15. The system according to claim 1, wherein said imaging device produces a three-dimensional image of the specimen.

16. The system according to claim 1, wherein said signal processor reconstructs the acoustic impedance in real time.

17. The system according to claim 16, wherein said imaging device updates the image of the specimen in real time.

18. The system according to claim 1, wherein the incident ultrasonic signal emitted by said transducer has a center frequency in the range between 3 and 5 MHz, inclusive, the incident ultrasonic signal imaging a field of view in a depth dimension of approximately 8 mm.

19. The system according to claim 1, wherein said imaging device includes at least one of a display and a printer.

20. The system according to claim 1, further comprising:
a memory adapted to store image information derived from the acoustic impedance reconstructed by said signal processor.

21. The system according to claim 1, further comprising:
a transmitter for transmitting image information to a remote location over at least one of: a fiber optic medium, a wire and free space.

22. A method of generating an ultrasound image, comprising the steps of:
 a) emitting an incident ultrasonic signal toward a specimen;
 b) receiving a reflection of the incident ultrasonic signal from the specimen and generating an electrical signal which represents a reflected ultrasonic signal;
 c) computing a Fourier transform of the electrical signal which represents the reflected ultrasonic signal to obtain a reflected signal spectrum;
 d) dividing the reflected signal spectrum by a spectrum of the incident ultrasonic signal to obtain a transfer function;
 e) applying a frequency-domain window function having a sharp, low-frequency cutoff to the transfer function;
 f) computing an inverse Fourier transform of the windowed transfer function to obtain an impulse response;
 g) calculating an acoustic impedance profile from the impulse response; and
 h) forming an image of the specimen in accordance with the acoustic impedance profile.

23. The method according to claim 22, wherein step f) includes integrating and exponentiating the impulse response in accordance with a plane wave Born approximation to obtain the acoustic impedance.

24. The method according to claim 22, wherein step e) includes reducing to zero a magnitude of a DC component of the transfer function.

25. The method according to claim 24, wherein step e) includes not attenuating a magnitude of at least one of: a lowest frequency component above the DC component of the transfer function, a second lowest frequency component of the transfer function and a third lowest frequency component of the transfer function.

26. The method according to claim 25, wherein step e) includes not attenuating a magnitude of the lowest frequency component of the transfer function.

27. The method according to claim 22, wherein the window function applied in step e) is a rectangular filter having a sharp, high-frequency cutoff corresponding to a high-frequency end of the incident ultrasonic signal.

28. The method according to claim 22, wherein the window function applied in step e) smoothly approaches zero at a high-frequency end, such that magnitudes of high-frequency components of the transfer function are gradually attenuated to zero with increasing frequency.

29. The method according to claim 22, further comprising the step of:
 i) applying a time domain pre-filter to the reflected electrical signal prior to computing the Fourier transform of the reflected electrical signal.

30. The method according to claim 22, further comprising the step of:
 i) effecting a scan by repeating steps a) through g) along a plurality of different, adjacent paths within the specimen, wherein step h) includes forming an image using the acoustic impedance calculated for each of the plurality of paths.

31. The method according to claim 30, wherein step i) includes controlling a direction of the incident ultrasonic signal by setting relative phases of a phased-array of transducer elements.

32. The method according to claim 31, wherein step i) includes scanning in at least one of the following scanning formats: linear; steered linear, sector, and circular.

33. The method according to claim 30, wherein step i) includes mechanically displacing a transducer to effect scanning.

34. The method according to claim 30, wherein the plurality of paths form a plane in the specimen, and wherein step h) includes forming a two-dimensional B-scan image of the specimen.

35. The method according to claim 22, wherein step h) includes forming a three-dimensional image of the specimen.

36. The method according to claim 22, wherein steps c) through h) are performed in real time.

37. The method according to claim 22, wherein step a) includes emitting the incident ultrasonic signal having a center frequency in the range between 3 and 5 MHz, inclusive.

38. The method according to claim 22, further comprising the steps of:
 i) prior to step h), determining whether the acoustic impedance profile meets a predetermined requirement;
 j) when the acoustic impedance profile fails to meet the predetermined requirement, constraining values of certain components of the acoustic impedance profile;
 k) computing amplitudes of low frequency components of the transfer function below the sharp, low-frequency cutoff from the constrained values of the certain components of the acoustic impedance profile;
 l) repeating steps f), g), i), j) and k) at most L times, where L is a positive integer, or until the acoustic impedance profile meets the predetermined requirement in step i).

39. The method according to claim 38, wherein:
the predetermined requirements is that the value of all of the components of the acoustic impedance profile be at least 1.0; and
step j) includes: dividing the acoustic impedance profile into N regions, where N is an integer greater than 1; for each region, identifying a component of the acoustic impedance profile having a minimum value within the region; for each region, if the minimum value is less than 1.0, constraining the value of the identified component in the region to a value no less than 1.0.

40. The method according to claim 22, further comprising the step of:
 i) prior to step f), adjusting amplitudes of components of the transfer function to compensate for attenuation caused by intervening tissue.

41. An ultrasound imaging system, comprising:
a transducer adapted to emit an incident ultrasonic signal toward a specimen, said transducer receiving a reflection of the incident ultrasonic signal from the specimen and generating an electrical signal which represents a reflected ultrasonic signal;
a signal processor which reconstructs an acoustic impedance of a portion of the specimen through which the reflected ultrasonic signal passes by:
 a) computing a Fourier transform of the electrical signal which represents the reflected ultrasonic signal to obtain a reflected signal spectrum;

b) dividing the reflected signal spectrum by a spectrum of the incident ultrasonic signal to obtain a transfer function;

c) applying a frequency-domain window function having a sharp, low-frequency cutoff to the transfer function;

d) computing an inverse Fourier transform of the windowed transfer function to obtain an impulse response;

e) calculating an acoustic impedance profile from the impulse response;

f) determining whether the acoustic impedance profile meets a predetermined requirement;

g) when the acoustic impedance profile fails to meet the predetermined requirement, constraining values of certain components of the acoustic impedance profile;

h) computing amplitudes of low-frequency components of the transfer function below the sharp, low-frequency cutoff from the constrained values of the certain components of the acoustic impedance profile; and i) repeating steps d) through h) at most L times, where L is a positive integer, or until the acoustic impedance profile meets the predetermined requirement in step f); and an imaging device adapted to form an image of the specimen in accordance with the acoustic impedance profile.

42. The apparatus according to claim 41, wherein:

the predetermined requirements include the requirement that the value of all of the components of the acoustic impedance profile be at least 1.0; and step g) includes: dividing the acoustic impedance profile into N regions, where N is an integer greater than 1; for each region, identifying a component of the acoustic impedance profile having a minimum value within the region; for each region, if the minimum value is less than 1.0, constraining the value of the identified component in the region to a value no less than 1.0.

* * * * *